United States Patent [19]

Nishimoto

[11] Patent Number: 5,578,451
[45] Date of Patent: Nov. 26, 1996

[54] METHODS AND SYSTEMS FOR SCREENING POTENTIAL ALZHEIMER'S DISEASE THERAPEUTICS

[75] Inventor: Ikuo Nishimoto, Brookline, Mass.

[73] Assignee: The General Hospital Corporation, Boston, Mass.

[21] Appl. No.: 371,930

[22] Filed: Jan. 12, 1995

Related U.S. Application Data

[63] Continuation of Ser. No. 19,208, Feb. 18, 1993, abandoned.

[51] Int. Cl.$^6$ .......................... G01N 33/53; G01N 33/567
[52] U.S. Cl. ..................... 435/7.1; 435/7.2; 435/7.21; 435/975
[58] Field of Search ............................... 435/6, 7.2, 7.21, 435/7.1; 436/518, 536

[56] References Cited

PUBLICATIONS

Bodor et al., "A Strategy for Delivery of Peptides into the Central Nervous System by Sequential Metabolism", Science 257:1698–1700, 1992.
Dyrks et al., "Identification, Transmembrane Orientation and Biogenesis of the Amyloid A4 Precursor of Alzheimer's Disease", EMBO J. 7:949–957, 1988.
Glenner et al., "Alzheimer's Disease: Initial Report of the Purification and Characterization of a Novel Cerebrovascular Amyloid Protein", Biochem Biophys. Res. Commun. 120:885–890, 1984.
Goate et al., "Segregation of a Missense Mutation in the Mykloid Precursor Protein Gene with Familial Alzheimer's Disease", Nature 349:704–706, 1991.
Granneman et al., "Developmental Expression of $G_o$ in Neuronal Cultures from Rat Mesencephalon and Hypothalamus", J. Neurochemistry 54:1995–2001, 1990.
Guillen et al., "A $G_o$–Like Protein in *Drosophila Melanogaster* and Its Expression in Memory Mutants", EMBO J. 9:1449–1455, 1990.
Higashijima et al., "Mastoparan, A Peptide Toxin from Wasp Venom, Mimics Receptors by Activating GTP–Binding Regulatory Proteins (G Proteins)", J. Biol. Chem. 263:6491–6494, 1988.
Kametani et al., "Demonstration of a 72 K β–Protein Precursos Fragment in Alzheimer and Normal Aged Brain", Biomedical Research 10:179–183, 1989.
Kang et al., "The Precursor of Alzheimer's Disease Amyloid A4 Protein Resembles a Cell–Surface Receptor", Nature 325:733–736, 1987.
Katada et al., "A New GTP–Binding Protein in Brain Tissues Serving as the Specific Substrate of Islet–Activating Protein, Pertussis Toxin", 213:353–358, 1987.
Kaziro, Ch. 11, "Structures of the Genes Coding for the α Subunits of G Proteins", In ADP–Ribosylating Toxins and G Proteins, pp. 189–206, 1988.
Kitaguchi et al., "Novel Precursors of Alzheimer's Disease Amyloid Protein Shows Protease Inhibitory Activity", Nature 331:530–532, 1988.

Matsui et al., "Nucleotide and Deduced Amino Acid Sequences of a GTP–Binding Protein Family with Molecular Weights of 25,000 from Bovine Brain", J. Biol. Chem. 263:11071–4, 1988.
Morishita et al., "Purification and Indentification of Two Pertussis–Toxin–Sensitive GTP–Binding Proteins of Bovine Spleen", Bio. and Biophys Research Comm. 161:1280–1285, 1989.
Nishimoto et al., "Possible Direct Linkage of Insulin–Like Growth Factor–II Receptor with Guanine Nucleotide–Binding Proteins", J. Biol. Chem. 264:14029–14038, 1989.
Okamoto et al., "Analysis of Stimulation–G Protein Subunit Coupling by Using Active Insulin–Like Growth Factor II Receptor Peptide", Proc. Natl. Acad. Sci. USA 88:8020–8023, 1991.
Okamoto et al., "A Simple Structure Encodes G Protein–Activating Function of the IGF–II/Mannose 6–Phosphate Receptor", Cell 62:709–717, 1990.
Ponte et al., "A New A4 Amyloid mRNA Contains a Domain Homologous to Serine Proteinase Inhibitors", Nature 331:525–527, 1988.
Ranty et al., "Truncation of Ribulose–1, 5–Bisphosphate Carboxylase/Oxygenase (Rubisco) from *Rhodospirillum rubrum* Affects the Holoenzyme Assembly and Activity", EMBO J. 9:1365–1373, 1990.
Selkoe et al., "Amyloid β Protein Precursor and the Pathogenesis of Alzheimer's Disease", Cell 58:611–612, 1989.
Shivers et al., "Alzheimer's Disease Amyloidogenic Glycoprotein:Expression Pattern in Rat Brain Suggests a Role in Cell Contact", EMBO J. 7:1365–1370, 1988.
Strathmann et al., "Alternative Splicing Produces Transcripts Encoding Two Forms of the α Subunit of GTP–Binding Protein $G_o$", Proc. Natl. Acad. Sci. USA 87:6477–6481, 1990.
Strittmatter et al., "$G_o$ is a Major Growth Cone Protein Subject to Regulation by GAP–43", Nature 344:836–841, 1990.
Strittmatter et al., "The Neuronal Growth Cone as a Specialized Transduction System", Bioessays 13:127–134, 1990.

(List continued on next page.)

*Primary Examiner*—Marian C. Knode
*Assistant Examiner*—Patricia A. Duffy
*Attorney, Agent, or Firm*—Fish & Richardson P.C.

[57] ABSTRACT

A method of identifying a therapeutic useful for treating or preventing Alzheimer's disease, which method includes the steps of contacting (a) a first molecule containing the couplone portion of APP (SEQ ID NO: 1) with (b) a second molecule containing the amino acid sequence of $G_o$ (SEQ ID NO: 2) or an APP-associating region of $G_o$ (SEQ ID NOs: 3, 4, or 5), in the presence of a candidate compound; and determining whether the candidate compound interferes with the association of the first and second molecules, such interference being an indication that the candidate compound is a potential Alzheimer's disease therapeutic.

20 Claims, 12 Drawing Sheets

PUBLICATIONS

Tanzi et al., "Protease Inhibitor Domain Encoded by an Amyloid Protein Precursor mRNA Associated with Alzheimer's Disease", Nature 331:528–530, 1988.

Weldemann et al., "Indentification, Biogenesis, and Localization of Precursors of Alzheimer's Disease A4 Amyloid Protein", Cell 57:115–126, 1989.

Yamada et al., "Complementary DNA for Themouse Homolog of the Human Amyloid Beta Protein Precursor", Biochem. Biophys. Res. Commun. 149:665–671, 1987.

Yankner et al., "Neurotoxicity of a Fragment of the Amyloid Precursor Associated with Alzheimer's Disease", Science 245:417–420, 1989.

Ui et al., Islet–Activating Protein, Pertussis Toxin: A Specific Uncoupler of Receptor–Mediated Inhibition of Adenylate Cyclase, Advances in Cyclic Nucleotide and Protein Phosphorylation Research 17:145–151, 1984.

Klausner, R. D., et al., "Protein Degradation in the Endoplasmic Reticulum", 1990, *Cell*, vol. 62, pp. 611–614.

*Peptide Inhibitors of ADP–Ribosylation by Pertussis Toxin Are Substrates with Affinities Comparable to Those of the Trimeric GTP–Binding Proteins*, Molecular Pharmacology, 42:760–764, 1992, Rolf Graf et al.

Gunnersen et al., Preliminary Characterization of a Novel Alzheimer's Disease Protein, FASEB Journal 5:A456, abstract 494, 1991.

Lemaire et al., The PreA4(695) Precursor Protein of Alzheimer's Disease A4 Amyloid is Encoded by 16 Exons, Nucleic Acids Research 17:517–522, 1989.

Nishimoto et al., Alzheimer amyloid precursor complexes with brain GTP–binding protein $G_o$. Nature 362 (6415): 74–79. 1993.

```
TGTGGCAGGG AAGGGGCCAC C ATG GGA TGT ACG CTG AGC GCA GAG GAG AGA           51
                         Met Gly Cys Thr Leu Ser Ala Glu Glu Arg
                         1            5                       10

GCC GCC CTC GAG CGG AGC AAG GCG ATT GAG AAA AAC CTA AAA GAA GAT           99
Ala Ala Leu Glu Arg Ser Lys Ala Ile Glu Lys Asn Leu Lys Glu Asp
                15                  20                  25

GGC ATC AGC GCC GCC AAA GAC GTG AAA TTA CTC CTG CTG GGG GCT GGA          147
Gly Ile Ser Ala Ala Lys Asp Val Lys Leu Leu Leu Leu Gly Ala Gly
            30                  35                  40

GAA TCA GGA AAA AGC ACC ATT GTG AAG CAG ATG AAG ATC ATC CAT GAA          195
Glu Ser Gly Lys Ser Thr Ile Val Lys Gln Met Lys Ile Ile His Glu
        45                  50                  55

GAT GGC TTC TCT GGG GAA GAC GTG AAG CAG TAC AAG CCT GTG GTC TAC          243
Asp Gly Phe Ser Gly Glu Asp Val Lys Gln Tyr Lys Pro Val Val Tyr
    60                  65                  70

AGC AAC ACC ATC CAG TCT CTG GCG GCC ATT GTC CGG GCC ATG GAC ACT          291
Ser Asn Thr Ile Gln Ser Leu Ala Ala Ile Val Arg Ala Met Asp Thr
75                  80                  85                  90

TTG GGC GTG GAG TAT GGT GAC AAG GAG AGG AAG ACG GAC TCC AAG ATG          339
Leu Gly Val Glu Tyr Gly Asp Lys Glu Arg Lys Thr Asp Ser Lys Met
                95                  100                 105

GTG TGT GAC GTG GTG AGT CGT ATG GAA GAC ACT GAA CCG TTC TCT GCA          387
Val Cys Asp Val Val Ser Arg Met Glu Asp Thr Glu Pro Phe Ser Ala
            110                 115                 120

GAA CTT CTT TCT GCC ATG ATG CGA CTC TGG GGC GAC TCG GGG ATC CAG          435
Glu Leu Leu Ser Ala Met Met Arg Leu Trp Gly Asp Ser Gly Ile Gln
        125                 130                 135

GAG TGC TTC AAC CGA TCT CGG GAG TAT CAG CTC AAT GAC TCT GCC AAA          483
Glu Cys Phe Asn Arg Ser Arg Glu Tyr Gln Leu Asn Asp Ser Ala Lys
    140                 145                 150

TAC TAC CTG GAC AGC CTG GAT CGG ATT GGA GCC GGT GAC TAC CAG CCC          531
Tyr Tyr Leu Asp Ser Leu Asp Arg Ile Gly Ala Gly Asp Tyr Gln Pro
155                 160                 165                 170

ACT GAG CAG GAC ATC CTC CGA ACC AGA GTC AAA ACA ACT GGC ATC GTA          579
Thr Glu Gln Asp Ile Leu Arg Thr Arg Val Lys Thr Thr Gly Ile Val
                175                 180                 185

GAA ACC CAC TTC ACC TTC AAG AAC CTC CAC TTC AGG CTG TTT GAC GTC          627
Glu Thr His Phe Thr Phe Lys Asn Leu His Phe Arg Leu Phe Asp Val
            190                 195                 200

GGG GGC CAG CGA TCT GAA CGC AAG AAG TGG ATC CAC TGC TTT GAG GAT          675
Gly Gly Gln Arg Ser Glu Arg Lys Lys Trp Ile His Cys Phe Glu Asp
        205                 210                 215

GTC ACG GCC ATC ATC TTC TGT GTC GCA CTC AGC GGC TAT GAC CAG GTG          723
Val Thr Ala Ile Ile Phe Cys Val Ala Leu Ser Gly Tyr Asp Gln Val
    220                 225                 230

CTC CAC GAG GAC GAA ACC ACG AAC CGC ATG CAC GAG TCT CTC ATG CTC          771
Leu His Glu Asp Glu Thr Thr Asn Arg Met His Glu Ser Leu Met Leu
235                 240                 245                 250
```

FIG. 4A-1

```
TTC GAC TCC ATC TGT AAC AAC AAG TTT TTC ATT GAT ACC TCC ATC ATC    819
Phe Asp Ser Ile Cys Asn Asn Lys Phe Phe Ile Asp Thr Ser Ile Ile
            255             260                 265

CTC TTC CTC AAC AAG AAA GAC CTC TTT GGC GAG AAG ATT AAG AAG TCA    867
Leu Phe Leu Asn Lys Lys Asp Leu Phe Gly Glu Lys Ile Lys Lys Ser
            270             275                 280

CCC TTG ACC ATC TGC TTT CCC GAA TAC CCA GGC TCC AAC ACC TAT GAA    915
Pro Leu Thr Ile Cys Phe Pro Glu Tyr Pro Gly Ser Asn Thr Tyr Glu
            285             290                 295

GAT GCA GCT GCC TAC ATC CAA ACA CAG TTT GAA AGC AAA AAC CGC TCA    963
Asp Ala Ala Ala Tyr Ile Gln Thr Gln Phe Glu Ser Lys Asn Arg Ser
300             305                 310

CCC AAC AAA GAA ATT TAC TGT CAC ATG ACT TGT GCC ACA GAC ACG AAT   1011
Pro Asn Lys Glu Ile Tyr Cys His Met Thr Cys Ala Thr Asp Thr Asn
315             320                 325                 330

AAT ATC CAG GTG GTA TTC GAC GCC GTC ACC GAC ATC ATC ATT GCC AAC   1059
Asn Ile Gln Val Val Phe Asp Ala Val Thr Asp Ile Ile Ile Ala Asn
                335                 340                 345

AAT CTC CGG GGC TGC GGC TTG TAC TGACCTCTTG TCCTGTATAG CAACCTATTT   1113
Asn Leu Arg Gly Cys Gly Leu Tyr
            350

GACTGCTTCA TGGACTCTTT GCTGTTGATG TTGATCTCCT GGTAGCATGA CCTTTGGCCT 1173
TTGTAAGACA CACAGCCTTT CTGTACCAAG CCCCTGTCTA ACCTACGACC CAGAGTGAC  1233
TGACGGCTGT GTATTCTGT AGAATGCTGT AGAATACAGT TTTAGTTGAG TCTTTACATT  1293
TAGAACTTGA AAGGATTTTA AAAAACAAAA CAAAAACCAT TTCTCATGTG CTTTGTAGCT 1353
TTAAAGAAA AAAGGAAAAC TCACCATTTA ATCCATATTT CCTTTTTATT TTGAAGTTTA  1413
AAAAAAAAAT GTCTGTACCC ACACCCTCCC CCTTCCCCAC CTCAGCAGAA CTGGGGCTGG 1473
CACACAGAGG CAGTGCTGGG CCTGGCGCCT CCCAGGGCTT CTGTGCAGCC CATGGCTGGT 1533
GGGAACATGT CAGGCTAGTC TGTCTAGAAG GCCACTGGCC ACTGTACCCA CCCTTCCCCA 1593
TGCCTGTGGG CTGCCCAGAC ACCTCATATA CCACCAGGCA GTGGCAGCTC CGCCCTGCTC 1653
AGCCATGCGA CTCCAAACAC ACTCAAAGTT TGCGTAGAAA AAGCACAGCT CTGGCAGGGG 1713
TAGCTGCCAC AGACAACGCT CATCACCTAT AGAAATCCAG CCCTATAGAA GCAATTCACC 1773
CAGCCCCTTC CTACACTCCC TTTGTGTTGT TAACTTTTTG GTTTTTCTGG TCCTAGTGAG 1833
TGCCTCCCAT GCATACCTGA CCAGCTCTGC CAGTGTCTGG GGTCTGGGGA ACAGGGGTTG 1893
TGTGGTTTGG TTTTTGG                                                1910
```

FIG. 4A-2

```
GCTGTGGCAG GGAAGGGGCC ACC ATG GGA TGT ACG CTG AGC GCA GAG GAG                50
                         Met Gly Cys Thr Leu Ser Ala Glu Glu
                          1               5

AGA GCC GCC CTC GAG CGG AGC AAG GCG ATT GAG AAA AAC CTC AAA GAA               98
Arg Ala Ala Leu Glu Arg Ser Lys Ala Ile Glu Lys Asn Leu Lys Glu
 10              15                  20                  25

GAT GGC ATC AGC GCC GCC AAA GAC GTG AAA TTA CTC CTG CTG GGG GCT              146
Asp Gly Ile Ser Ala Ala Lys Asp Val Lys Leu Leu Leu Leu Gly Ala
             30                  35                  40

GGA GAA TCA GGA AAA AGC ACC ATT GTG AAG CAG ATG AAG ATC ATC CAT              194
Gly Glu Ser Gly Lys Ser Thr Ile Val Lys Gln Met Lys Ile Ile His
                 45                  50                  55

GAA GAT GGC TTC TCT GGG GAA GAC GTG AAG CAG TAC AAG CCT GTG GTC              242
Glu Asp Gly Phe Ser Gly Glu Asp Val Lys Gln Tyr Lys Pro Val Val
             60                  65                  70

TAC AGC AAC ACC ATC CAG TCT CTG GCG GCC ATT GTC CGG GCC ATG GAC              290
Tyr Ser Asn Thr Ile Gln Ser Leu Ala Ala Ile Val Arg Ala Met Asp
     75                  80                  85

ACT TTG GGC GTG GAG TAT GGT GAC AAG GAG AGG AAG ACG GAC TCC AAG              338
Thr Leu Gly Val Glu Tyr Gly Asp Lys Glu Arg Lys Thr Asp Ser Lys
 90                  95                 100                 105

ATG GTG TGT GAC GTG GTG AGT CGT ATG GAA GAC ACT GAA CCG TTC TCT              386
Met Val Cys Asp Val Val Ser Arg Met Glu Asp Thr Glu Pro Phe Ser
                110                 115                 120

GCA GAA CTT CTT TCT GCC ATG ATG CGA CTC TGG GGC GAC TCG GGG ATC              434
Ala Glu Leu Leu Ser Ala Met Met Arg Leu Trp Gly Asp Ser Gly Ile
             125                 130                 135

CAG GAG TGC TTC AAC CGA TCT CGG GAG TAT CAG CTC AAT GAC TCT GCC              482
Gln Glu Cys Phe Asn Arg Ser Arg Glu Tyr Gln Leu Asn Asp Ser Ala
         140                 145                 150

AAA TAC TAC CTG GAC AGC CTG GAT CGG ATT GGA GCC GGT GAC TAC CAG              530
Lys Tyr Tyr Leu Asp Ser Leu Asp Arg Ile Gly Ala Gly Asp Tyr Gln
155                 160                 165

CCC ACT GAG CAG GAC ATC CTC CGA ACC AGA GTC AAA ACA ACT GGC ATC              578
Pro Thr Glu Gln Asp Ile Leu Arg Thr Arg Val Lys Thr Thr Gly Ile
170                 175                 180                 185

GTA GAA ACC CAC TTC ACC TTC AAG AAC CTC CAC TTC AGG CTG TTT GAC              626
Val Glu Thr His Phe Thr Phe Lys Asn Leu His Phe Arg Leu Phe Asp
                 190                 195                 200

GTC GGG GGC CAG CGA TCT GAA CGC AAG AAG TGG ATC CAC TGC TTT GAG              674
Val Gly Gly Gln Arg Ser Glu Arg Lys Lys Trp Ile His Cys Phe Glu
             205                 210                 215

GAT GTC ACG GCC ATC ATC TTC TGT GTC GCA CTC AGC GGC TAT GAC CAG              722
Asp Val Thr Ala Ile Ile Phe Cys Val Ala Leu Ser Gly Tyr Asp Gln
         220                 225                 230

GTG CTC CAC GAG GAC GAA ACC ACG AAC CGC ATG CAC GAA TCC CTG AAG              770
Val Leu His Glu Asp Glu Thr Thr Asn Arg Met His Glu Ser Leu Lys
     235                 240                 245
```

FIG. 4B-1

| | | | | | | | | | | | | | | | | |
|---|---|---|---|---|---|---|---|---|---|---|---|---|---|---|---|---|
|CTC|TTC|GAC|AGC|ATC|TGC|AAC|AAC|AAG|TGG|TTC|ACA|GAC|ACA|TCT|ATT|818|
|Leu|Phe|Asp|Ser|Ile|Cys|Asn|Asn|Lys|Trp|Phe|Thr|Asp|Thr|Ser|Ile| |
|250| | | | |255| | | |260| | | | |265| | |
|ATC|CTG|TTT|CTC|AAC|AAG|AAG|GAC|ATA|TTT|GAG|GAG|AAG|ATC|AAG|AAG|866|
|Ile|Leu|Phe|Leu|Asn|Lys|Lys|Asp|Ile|Phe|Glu|Glu|Lys|Ile|Lys|Lys| |
| | | | |270| | | |275| | | | |280| | | |
|TCC|CCA|CTC|ACC|ATC|TGC|TTT|CCT|GAA|TAC|ACA|CGC|CCC|AGT|GCC|TTC|914|
|Ser|Pro|Leu|Thr|Ile|Cys|Phe|Pro|Glu|Tyr|Thr|Gly|Pro|Ser|Ala|Phe| |
| | | |285| | | |290| | | | |295| | | | |
|ACA|GAA|GCT|GTG|GCT|CAC|ATC|CAA|GGG|CAG|TAT|GAG|AGT|AAG|AAT|AAG|962|
|Thr|Glu|Ala|Val|Ala|His|Ile|Gln|Gly|Gln|Tyr|Glu|Ser|Lys|Asn|Lys| |
| | |300| | | |305| | | |310| | | | | | |
|TCA|GCT|CAC|AAG|GAA|GTC|TAC|AGC|CAT|GTC|ACC|TGT|GCC|ACG|GAC|ACC|1010|
|Ser|Ala|His|Lys|Glu|Val|Tyr|Ser|His|Val|Thr|Cys|Ala|Thr|Asp|Thr| |
| |315| | | |320| | | |325| | | | | | | |
|AAC|AAC|ATC|CAA|TTC|GTC|TTT|GAT|GCC|GTG|ACA|GAT|GTC|ATC|ATC|GCC|1058|
|Asn|Asn|Ile|Gln|Phe|Val|Phe|Asp|Ala|Val|Thr|Asp|Val|Ile|Ile|Ala| |
|330| | | |335| | | |340| | | | |345| | | |
|AAA|AAC|CTA|CGG|GGC|TGT|GGA|CTC|TAC|TGAGCCCTGG|CCTCCTACCC| | | | |1105|
|Lys|Asn|Leu|Arg|Gly|Cys|Gly|Leu|Tyr| | | | | | | | |
| | | |350| | | | | | | | | | | | | |

```
AGCCTGCCAC TCACTCCTCC CCTGGACCCA GAGCTCTGTC ACTGCTCAGA TGCCCTGTTA 1165
ACTGAAGAAA ACCTGGAGGC TAGCCTTGGG GGCAGGAGGA GGCATCCTTT GAGCATCCCC 1225
ACCCCACCCA ACTTCAGCCT CGTGACACGT GGGAACAGGG TTGGGCAGAG GTGTGGAACA 1285
GCACAAGGCC AGAGACCACG GCATGCCACT TGGGTGCTGC TCACTGGTCA GCTGTGTGTC 1345
TTACACAGAG GCCGAGTGGG CAACACTGCC ATCTGATTCA GAATGGGCAT GCCCTGTCCT 1405
CTGTACCTCT TGTTCAGTGT CCTGGTTTCT CTTCCACCTT GGTGATAGGA TGGCTGGCAG 1465
GAAGGCCCCA TGGAAGGTGC TGCTTGATTA GGGGATAGTC GATGGCATCT CTCAGCAGTC 1525
CTCAGGGTCT GTTTGGTAGA GGGTGGTTTC GTCGACAAAA GCCAACATGG AATCAGGCCA 1585
CTTTTGGGGC GCAAAGACTC AGACTTTGGG GACGGGTTCC CTCCTCCTTC ACTTTGGATC 1645
TTGGCCCCTC TCTGGTCATC TTCCCTTGCC CTTGGGCTCC CCAGGATACT CAGCCCTGAC 1705
TCCCATGGGG TTGGGAATAT TCCTTAAGAC TGGCTGACTG CAAAGGTCAC CGATGGAGAA 1765
ACATCCCTGT GCTACAGAAT TGGGGGTGGG ACAGCTGAGG GGGCAGGCGG CTCTTTCCTG 1825
ATAGTTGATG ACAAGCCCTG AGAATGCCAT CTGCTGGCTC CACTCACACG GGCTCAACTG 1885
TCCTGGGTGA TAGTGACTTG CCAGGCCACA GGCTGCAGGT CACAGACAGA GCAGGCAAGC 1945
AGCCTTGCAA CTGCAGATTA CTTAGGGAGA AGCATCCTAG CCCCAGCTAA CTTTGGACAG 2005
TCAGCATATG TCCCTGCCAT CCCTAGACAT CTCCAGTCAG CTGGTATCAC AGCCAGTGGT 2065
TCAGACAGGT TTGAATGCTC ATGTGGCAGG GGGCCCGGTA CCCAGCTTTT GTTCCCTTTA 2125
GTGAGGGTTA ATTGCGCGCT TGGGCTAATC ATGGTCATAG CTGTTGGGCG TTGCTGGCGT 2185
TTTTCCATAG GCTCCGCCCC CTGACGAGAT CACAAAAATC GACGCTCAAG TCAGAGGTGG 2245
CGAAACCGAC AGACTATAAG ATACCAGGC                                  2274
```

FIG. 4B-2

SEQUENCE LISTING ( 1 ) GENERAL INFORMATION:

( i i i ) NUMBER OF SEQUENCES: 30

( 2 ) INFORMATION FOR SEQ ID NO: 1:

( i ) SEQUENCE CHARACTERISTICS:
        ( A ) LENGTH: 20
        ( B ) TYPE: amino acid
        ( C ) STRANDEDNESS:
        ( D ) TOPOLOGY: linear ( x i ) SEQUENCE DESCRIPTION: SEQ ID NO: 1:

```
His His Gly Val Val Glu Val Asp Ala Ala Val Thr Pro Glu Glu Arg
 1               5                  10                  15
His Leu Ser Lys
            20
```

( 2 ) INFORMATION FOR SEQ ID NO: 2:

( i ) SEQUENCE CHARACTERISTICS:
        ( A ) LENGTH: 1910
        ( B ) TYPE: nucleic acid
        ( C ) STRANDEDNESS: double
        ( D ) TOPOLOGY: linear ( x i ) SEQUENCE DESCRIPTION: SEQ ID NO: 2:

```
TGTGGCAGGG AAGGGGCCAC C ATG GGA TGT ACG CTG AGC GCA GAG GAG AGA          51
                         Met Gly Cys Thr Leu Ser Ala Glu Glu Arg
                          1           5                      10

GCC GCC CTC GAG CGG AGC AAG GCG ATT GAG AAA AAC CTA AAA GAA GAT          99
Ala Ala Leu Glu Arg Ser Lys Ala Ile Glu Lys Asn Leu Lys Glu Asp
             15                  20                  25

GGC ATC AGC GCC GCC AAA GAC GTG AAA TTA CTC CTG CTG GGG GCT GGA         147
Gly Ile Ser Ala Ala Lys Asp Val Lys Leu Leu Leu Leu Gly Ala Gly
             30                  35                  40

GAA TCA GGA AAA AGC ACC ATT GTG AAG CAG ATG AAG ATC ATC CAT GAA         195
Glu Ser Gly Lys Ser Thr Ile Val Lys Gln Met Lys Ile Ile His Glu
         45                  50                  55

GAT GGC TTC TCT GGG GAA GAC GTG AAG CAG TAC AAG CCT GTG GTC TAC         243
Asp Gly Phe Ser Gly Glu Asp Val Lys Gln Tyr Lys Pro Val Val Tyr
     60                  65                  70

AGC AAC ACC ATC CAG TCT CTG GCG GCC ATT GTC CGG GCC ATG GAC ACT         291
Ser Asn Thr Ile Gln Ser Leu Ala Ala Ile Val Arg Ala Met Asp Thr
 75                  80                  85                  90

TTG GGC GTG GAG TAT GGT GAC AAG GAG AGG AAG ACG GAC TCC AAG ATG         339
Leu Gly Val Glu Tyr Gly Asp Lys Glu Arg Lys Thr Asp Ser Lys Met
                 95                 100                 105

GTG TGT GAC GTG GTG AGT CGT ATG GAA GAC ACT GAA CCG TTC TCT GCA         387
Val Cys Asp Val Val Ser Arg Met Glu Asp Thr Glu Pro Phe Ser Ala
            110                 115                 120

GAA CTT CTT TCT GCC ATG ATG CGA CTC TGG GGC GAC TCG GGG ATC CAG         435
Glu Leu Leu Ser Ala Met Met Arg Leu Trp Gly Asp Ser Gly Ile Gln
        125                 130                 135

GAG TGC TTC AAC CGA TCT CGG GAG TAT CAG CTC AAT GAC TCT GCC AAA         483
Glu Cys Phe Asn Arg Ser Arg Glu Tyr Gln Leu Asn Asp Ser Ala Lys
    140                 145                 150

TAC TAC CTG GAC AGC CTG GAT CGG ATT GGA GCC GGT GAC TAC CAG CCC         531
Tyr Tyr Leu Asp Ser Leu Asp Arg Ile Gly Ala Gly Asp Tyr Gln Pro
155                 160                 165                 170

ACT GAG CAG GAC ATC CTC CGA ACC AGA GTC AAA ACA ACT GGC ATC GTA         579
```

| | | | | | | | | | | | | | | | |
|---|---|---|---|---|---|---|---|---|---|---|---|---|---|---|---|
| Thr | Glu | Gln | Asp | Ile | Leu | Arg | Thr | Arg | Val | Lys | Thr | Thr | Gly | Ile | Val |
|  |  |  |  | 175 |  |  |  | 180 |  |  |  |  |  | 185 |  |

| GAA | ACC | CAC | TTC | ACC | TTC | AAG | AAC | CTC | CAC | TTC | AGG | CTG | TTT | GAC | GTC | 627 |
|---|---|---|---|---|---|---|---|---|---|---|---|---|---|---|---|---|
| Glu | Thr | His | Phe | Thr | Phe | Lys | Asn | Leu | His | Phe | Arg | Leu | Phe | Asp | Val |  |
|  |  | 190 |  |  |  |  | 195 |  |  |  |  |  | 200 |  |  |  |

| GGG | GGC | CAG | CGA | TCT | GAA | CGC | AAG | AAG | TGG | ATC | CAC | TGC | TTT | GAG | GAT | 675 |
|---|---|---|---|---|---|---|---|---|---|---|---|---|---|---|---|---|
| Gly | Gly | Gln | Arg | Ser | Glu | Arg | Lys | Lys | Trp | Ile | His | Cys | Phe | Glu | Asp |  |
|  |  | 205 |  |  |  |  | 210 |  |  |  |  | 215 |  |  |  |  |

| GTC | ACG | GCC | ATC | ATC | TTC | TGT | GTC | GCA | CTC | AGC | GGC | TAT | GAC | CAG | GTG | 723 |
|---|---|---|---|---|---|---|---|---|---|---|---|---|---|---|---|---|
| Val | Thr | Ala | Ile | Ile | Phe | Cys | Val | Ala | Leu | Ser | Gly | Tyr | Asp | Gln | Val |  |
|  | 220 |  |  |  |  | 225 |  |  |  |  | 230 |  |  |  |  |  |

| CTC | CAC | GAG | GAC | GAA | ACC | ACG | AAC | CGC | ATG | CAC | GAG | TCT | CTC | ATG | CTC | 771 |
|---|---|---|---|---|---|---|---|---|---|---|---|---|---|---|---|---|
| Leu | His | Glu | Asp | Glu | Thr | Thr | Asn | Arg | Met | His | Glu | Ser | Leu | Met | Leu |  |
| 235 |  |  |  |  | 240 |  |  |  |  | 245 |  |  |  |  | 250 |  |

| TTC | GAC | TCC | ATC | TGT | AAC | AAC | AAG | TTT | TTC | ATT | GAT | ACC | TCC | ATC | ATC | 819 |
|---|---|---|---|---|---|---|---|---|---|---|---|---|---|---|---|---|
| Phe | Asp | Ser | Ile | Cys | Asn | Asn | Lys | Phe | Phe | Ile | Asp | Thr | Ser | Ile | Ile |  |
|  |  |  |  | 255 |  |  |  |  | 260 |  |  |  |  | 265 |  |  |

| CTC | TTC | CTC | AAC | AAG | AAA | GAC | CTC | TTT | GGC | GAG | AAG | ATT | AAG | AAG | TCA | 867 |
|---|---|---|---|---|---|---|---|---|---|---|---|---|---|---|---|---|
| Leu | Phe | Leu | Asn | Lys | Lys | Asp | Leu | Phe | Gly | Glu | Lys | Ile | Lys | Lys | Ser |  |
|  |  |  | 270 |  |  |  |  | 275 |  |  |  |  | 280 |  |  |  |

| CCC | TTG | ACC | ATC | TGC | TTT | CCC | GAA | TAC | CCA | GGC | TCC | AAC | ACC | TAT | GAA | 915 |
|---|---|---|---|---|---|---|---|---|---|---|---|---|---|---|---|---|
| Pro | Leu | Thr | Ile | Cys | Phe | Pro | Glu | Tyr | Pro | Gly | Ser | Asn | Thr | Tyr | Glu |  |
|  |  | 285 |  |  |  |  | 290 |  |  |  |  | 295 |  |  |  |  |

| GAT | GCA | GCT | GCC | TAC | ATC | CAA | ACA | CAG | TTT | GAA | AGC | AAA | AAC | CGC | TCA | 963 |
|---|---|---|---|---|---|---|---|---|---|---|---|---|---|---|---|---|
| Asp | Ala | Ala | Ala | Tyr | Ile | Gln | Thr | Gln | Phe | Glu | Ser | Lys | Asn | Arg | Ser |  |
| 300 |  |  |  |  | 305 |  |  |  |  | 310 |  |  |  |  |  |  |

| CCC | AAC | AAA | GAA | ATT | TAC | TGT | CAC | ATG | ACT | TGT | GCC | ACA | GAC | ACG | AAT | 1011 |
|---|---|---|---|---|---|---|---|---|---|---|---|---|---|---|---|---|
| Pro | Asn | Lys | Glu | Ile | Tyr | Cys | His | Met | Thr | Cys | Ala | Thr | Asp | Thr | Asn |  |
| 315 |  |  |  |  | 320 |  |  |  |  | 325 |  |  |  |  | 330 |  |

| AAT | ATC | CAG | GTG | GTA | TTC | GAC | GCC | GTC | ACC | GAC | ATC | ATC | ATT | GCC | AAC | 1059 |
|---|---|---|---|---|---|---|---|---|---|---|---|---|---|---|---|---|
| Asn | Ile | Gln | Val | Val | Phe | Asp | Ala | Val | Thr | Asp | Ile | Ile | Ile | Ala | Asn |  |
|  |  |  |  | 335 |  |  |  |  | 340 |  |  |  |  | 345 |  |  |

| AAT | CTC | CGG | GGC | TGC | GGC | TTG | TAC | TGACCTCTTG | TCCTGTATAG | CAACCTATTT | 1113 |
|---|---|---|---|---|---|---|---|---|---|---|---|
| Asn | Leu | Arg | Gly | Cys | Gly | Leu | Tyr |  |  |  |  |
|  |  |  |  |  | 350 |  |  |  |  |  |  |

| GACTGCTTCA | TGGACTCTTT | GCTGTTGATG | TTGATCTCCT | GGTAGCATGA | CCTTTGGCCT | 1173 |
|---|---|---|---|---|---|---|
| TTGTAAGACA | CACAGCCTTT | CTGTACCAAG | CCCTGTCTA | ACCTACGACC | CAGAGTGAC | 1233 |
| TGACGGCTGT | GTATTCTGT | AGAATGCTGT | AGAATACAGT | TTAGTTGAG | TCTTTACATT | 1293 |
| TAGAACTTGA | AAGGATTTTA | AAAACAAAA | CAAAAACCAT | TTCTCATGTG | CTTTGTAGCT | 1353 |
| TTAAAAGAAA | AAAGGAAAAC | TCACCATTTA | ATCCATATTT | CCTTTTATT | TTGAAGTTTA | 1413 |
| AAAAAAAAAT | GTCTGTACCC | ACACCCTCCC | CCTTCCCCAC | CTCAGCAGAA | CTGGGGCTGG | 1473 |
| CACACAGAGG | CAGTGCTGGG | CCTGGCGCCT | CCCAGGGCTT | CTGTGCAGCC | CATGGCTGGT | 1533 |
| GGGAACATGT | CAGGCTAGTC | TGTCTAGAAG | GCCACTGGCC | ACTGTACCCA | CCCTTCCCCA | 1593 |
| TGCCTGTGGG | CTGCCCAGAC | ACCTCATATA | CCACCAGGCA | GTGGCAGCTC | CGCCCTGCTC | 1653 |
| AGCCATGCGA | CTCCAAACAC | ACTCAAAGTT | TGCGTAGAAA | AAGCACAGCT | CTGGCAGGGG | 1713 |
| TAGCTGCCAC | AGACAACGCT | CATCACCTAT | AGAAATCCAG | CCCTATAGAA | GCAATTCACC | 1773 |
| CAGCCCCTTC | CTACACTCCC | TTTGTGTTGT | TAACTTTTTG | GTTTTCTGG | TCCTAGTGAG | 1833 |
| TGCCTCCCAT | GCATACCTGA | CCAGCTCTGC | CAGTGTCTGG | GGTCTGGGGA | ACAGGGGTTG | 1893 |
| TGTGGTTTGG | TTTTTGG |  |  |  |  | 1910 |

( 2 ) INFORMATION FOR SEQ ID NO: 3:

( i ) SEQUENCE CHARACTERISTICS:
        ( A ) LENGTH: 15

(B) TYPE: amino acid
        (C) STRANDEDNESS:
        (D) TOPOLOGY: linear (xi) SEQUENCE DESCRIPTION: SEQ ID NO: 3:

Asp Ala Val Thr Asp Ile Ile Ile Ala Lys Asn Leu Arg Gly Cys
 1               5                  10                  15

(2) INFORMATION FOR SEQ ID NO: 4:

(i) SEQUENCE CHARACTERISTICS:
        (A) LENGTH: 3
        (B) TYPE: amino acid
        (C) STRANDEDNESS:
        (D) TOPOLOGY: linear (xi) SEQUENCE DESCRIPTION: SEQ ID NO: 4:

Met Gly Cys
 1

(2) INFORMATION FOR SEQ ID NO: 5:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQ ID NO: 5:

Ile Glu Lys Asn Leu Lys Glu Asp Gly Ile Ser Ala Ala Lys Asp Val
 1               5                  10                  15

Lys Leu (2) INFORMATION FOR SEQ ID NO: 6:

(i) SEQUENCE CHARACTERISTICS:
        (A) LENGTH: 47
        (B) TYPE: amino acid
        (C) STRANDEDNESS:
        (D) TOPOLOGY: linear (xi) SEQUENCE DESCRIPTION: SEQ ID NO: 6:

Lys Lys Lys Gln Tyr Thr Ser Ile His His Gly Val Val Glu Val Asp
 1               5                  10                  15

Ala Ala Val Thr Pro Glu Glu Arg His Leu Ser Lys Met Gln Gln Asn
                20                  25                  30

Gly Tyr Glu Asn Pro Thr Tyr Lys Phe Phe Glu Gln Met Gln Asn
                35                  40                  45

(2) INFORMATION FOR SEQ ID NO: 7:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQ ID NO: 7:

Thr Val Ile Val Ile Thr Leu Val Met Leu
 1               5                  10

(2) INFORMATION FOR SEQ ID NO: 8:

(i) SEQUENCE CHARACTERISTICS:
        (A) LENGTH: 24
        (B) TYPE: amino acid
        (C) STRANDEDNESS:

(D) TOPOLOGY: linear (xi) SEQUENCE DESCRIPTION: SEQ ID NO: 8:

| Gly | Ala | Ile | Ile | Gly | Leu | Met | Val | Gly | Gly | Val | Val | Ile | Ala | Thr | Val |
|---|---|---|---|---|---|---|---|---|---|---|---|---|---|---|---|
| 1 | | | | 5 | | | | | 10 | | | | | 15 | |

| Ile | Val | Ile | Thr | Leu | Val | Met | Leu |
|---|---|---|---|---|---|---|---|
| | | | 20 | | | | |

(2) INFORMATION FOR SEQ ID NO: 9:

(i) SEQUENCE CHARACTERISTICS:
    (A) LENGTH: 2085
    (B) TYPE: nucleic acid
    (C) STRANDEDNESS: double
    (D) TOPOLOGY: linear (xi) SEQUENCE DESCRIPTION: SEQ ID NO: 9:

| ATG | CTG | CCC | GGT | TTG | GCA | CTG | CTC | CTG | CTG | GCC | GCC | TGG | ACG | GCT | CGG | 48 |
| Met | Leu | Pro | Gly | Leu | Ala | Leu | Leu | Leu | Leu | Ala | Ala | Trp | Thr | Ala | Arg | |
| 1 | | | | 5 | | | | | 10 | | | | | 15 | | |

| GCG | CTG | GAG | GTA | CCC | ACT | GAT | GGT | AAT | GCT | GGC | CTG | CTG | GCT | GAA | CCC | 96 |
| Ala | Leu | Glu | Val | Pro | Thr | Asp | Gly | Asn | Ala | Gly | Leu | Leu | Ala | Glu | Pro | |
| | | | 20 | | | | | 25 | | | | | 30 | | | |

| CAG | ATT | GCC | ATG | TTC | TGT | GGC | AGA | CTG | AAC | ATG | CAC | ATG | AAT | GTC | CAG | 144 |
| Gln | Ile | Ala | Met | Phe | Cys | Gly | Arg | Leu | Asn | Met | His | Met | Asn | Val | Gln | |
| | | 35 | | | | | 40 | | | | | 45 | | | | |

| AAT | GGG | AAG | TGG | GAT | TCA | GAT | CCA | TCA | GGG | ACC | AAA | ACC | TGC | ATT | GAT | 192 |
| Asn | Gly | Lys | Trp | Asp | Ser | Asp | Pro | Ser | Gly | Thr | Lys | Thr | Cys | Ile | Asp | |
| | 50 | | | | | 55 | | | | | 60 | | | | | |

| ACC | AAG | GAA | GGC | ATC | CTG | CAG | TAT | TGC | CAA | GAA | GTC | TAC | CCT | GGA | CTG | 240 |
| Thr | Lys | Glu | Gly | Ile | Leu | Gln | Tyr | Cys | Gln | Glu | Val | Tyr | Pro | Gly | Leu | |
| 65 | | | | | 70 | | | | | 75 | | | | | 80 | |

| CAG | ATC | ACC | AAT | GTG | GTA | GAA | GCC | AAC | CAA | CCA | GTG | ACC | ATC | CAG | AAC | 288 |
| Gln | Ile | Thr | Asn | Val | Val | Glu | Ala | Asn | Gln | Pro | Val | Thr | Ile | Gln | Asn | |
| | | | | 85 | | | | | 90 | | | | | 95 | | |

| TGG | TGC | AAG | CGG | GGC | CGC | AAG | CAG | TGC | AAG | ACC | CAT | CCC | CAC | TTT | GTG | 336 |
| Trp | Cys | Lys | Arg | Gly | Arg | Lys | Gln | Cys | Lys | Thr | His | Pro | His | Phe | Val | |
| | | | 100 | | | | | 105 | | | | | 110 | | | |

| ATT | CCC | TAC | CGC | TGC | TTA | GTT | GGT | GAG | TTT | GTA | AGT | GAT | GCC | CTT | CTC | 384 |
| Ile | Pro | Tyr | Arg | Cys | Leu | Val | Gly | Glu | Phe | Val | Ser | Asp | Ala | Leu | Leu | |
| | | | 115 | | | | | 120 | | | | | 125 | | | |

| GTT | CCT | GAC | AAG | TGC | AAA | TTC | TTA | CAC | CAG | GAG | AGG | ATG | GAT | GTT | TGC | 432 |
| Val | Pro | Asp | Lys | Cys | Lys | Phe | Leu | His | Gln | Glu | Arg | Met | Asp | Val | Cys | |
| | | | 130 | | | | | 135 | | | | | 140 | | | |

| GAA | ACT | CAT | CTT | CAC | TGG | CAC | ACC | GTC | GCC | AAA | GAG | ACA | TGC | AGT | GAG | 480 |
| Glu | Thr | His | Leu | His | Trp | His | Thr | Val | Ala | Lys | Glu | Thr | Cys | Ser | Glu | |
| 145 | | | | | 150 | | | | | 155 | | | | | 160 | |

| AAG | AGT | ACC | AAC | TTG | CAT | GAC | TAC | GGC | ATG | TTG | CTG | CCC | TGC | GGA | ATT | 528 |
| Lys | Ser | Thr | Asn | Leu | His | Asp | Tyr | Gly | Met | Leu | Leu | Pro | Cys | Gly | Ile | |
| | | | | 165 | | | | | 170 | | | | | 175 | | |

| GAC | AAG | TTC | CGA | GGG | GTA | GAG | TTT | GTG | TGT | TGC | CCA | CTG | GCT | GAA | GAA | 576 |
| Asp | Lys | Phe | Arg | Gly | Val | Glu | Phe | Val | Cys | Cys | Pro | Leu | Ala | Glu | Glu | |
| | | | 180 | | | | | 185 | | | | | 190 | | | |

| AGT | GAC | AAT | GTG | GAT | TCT | GCT | GAT | GCG | GAG | GAG | GAT | GAC | TGC | GAT | GTC | 624 |
| Ser | Asp | Asn | Val | Asp | Ser | Ala | Asp | Ala | Glu | Glu | Asp | Asp | Cys | Asp | Val | |
| | | | 195 | | | | | 200 | | | | | 205 | | | |

| TGG | TGG | GGC | GGA | GCA | GAC | ACA | GAC | TAT | GCA | GAT | GGG | AGT | GAA | GAC | AAA | 672 |
| Trp | Trp | Gly | Gly | Ala | Asp | Thr | Asp | Tyr | Ala | Asp | Gly | Ser | Glu | Asp | Lys | |
| | | 210 | | | | | 215 | | | | | 220 | | | | |

| GTA | GTA | GAA | GTA | GCA | GAG | GAG | GAA | GAA | GTG | GCT | GAG | GTG | GAA | GAA | GAA | 720 |
| Val | Val | Glu | Val | Ala | Glu | Glu | Glu | Glu | Val | Ala | Glu | Val | Glu | Glu | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GAA | GCC | GAT | GAT | GAC | GAG | GAC | GAT | GAG | GAT | GGT | GAT | GAG | GTA | GAG | GAA | 768 |
| Glu | Ala | Asp | Asp | Asp | Glu | Asp | Asp | Glu | Asp | Gly | Asp | Glu | Val | Glu | Glu | |
| | | | | 245 | | | | 250 | | | | | | 255 | | |
| GAG | GCT | GAG | GAA | CCC | TAC | GAA | GAA | GCC | ACA | GAG | AGA | ACC | ACC | AGC | ATT | 816 |
| Glu | Ala | Glu | Glu | Pro | Tyr | Glu | Glu | Ala | Thr | Glu | Arg | Thr | Thr | Ser | Ile | |
| | | | 260 | | | | | 265 | | | | | 270 | | | |
| GCC | ACC | ACC | ACC | ACC | ACC | ACC | ACA | GAG | TCT | GTG | GAA | GAG | GTG | GTT | CGA | 864 |
| Ala | Thr | Thr | Thr | Thr | Thr | Thr | Thr | Glu | Ser | Val | Glu | Glu | Val | Val | Arg | |
| | | 275 | | | | | 280 | | | | | 285 | | | | |
| GTT | CCT | ACA | ACA | GCA | GCC | AGT | ACC | CCT | GAT | GCC | GTT | GAC | AAG | TAT | CTC | 912 |
| Val | Pro | Thr | Thr | Ala | Ala | Ser | Thr | Pro | Asp | Ala | Val | Asp | Lys | Tyr | Leu | |
| | 290 | | | | 295 | | | | | 300 | | | | | | |
| GAG | ACA | CCT | GGG | GAT | GAG | AAT | GAA | CAT | GCC | CAT | TTC | CAG | AAA | GCC | AAA | 960 |
| Glu | Thr | Pro | Gly | Asp | Glu | Asn | Glu | His | Ala | His | Phe | Gln | Lys | Ala | Lys | |
| 305 | | | | 310 | | | | 315 | | | | | 320 | | | |
| GAG | AGG | CTT | GAG | GCC | AAG | CAC | CGA | GAG | AGA | ATG | TCC | CAG | GTC | ATG | AGA | 1008 |
| Glu | Arg | Leu | Glu | Ala | Lys | His | Arg | Glu | Arg | Met | Ser | Gln | Val | Met | Arg | |
| | | | | 325 | | | | 330 | | | | | 335 | | | |
| GAA | TGG | GAA | GAG | GCA | GAA | CGT | CAA | GCA | AAG | AAC | TTG | CCT | AAA | GCT | GAT | 1056 |
| Glu | Trp | Glu | Glu | Ala | Glu | Arg | Gln | Ala | Lys | Asn | Leu | Pro | Lys | Ala | Asp | |
| | | | 340 | | | | | 345 | | | | | 350 | | | |
| AAG | AAG | GCA | GTT | ATC | CAG | CAT | TTC | CAG | GAG | AAA | GTG | GAA | TCT | TTG | GAA | 1104 |
| Lys | Lys | Ala | Val | Ile | Gln | His | Phe | Gln | Glu | Lys | Val | Glu | Ser | Leu | Glu | |
| | | 355 | | | | | 360 | | | | | 365 | | | | |
| CAG | GAA | GCA | GCC | AAC | GAG | AGA | CAG | CAG | CTG | GTG | GAG | ACA | CAC | ATG | GCC | 1152 |
| Gln | Glu | Ala | Ala | Asn | Glu | Arg | Gln | Gln | Leu | Val | Glu | Thr | His | Met | Ala | |
| | 370 | | | | | 375 | | | | | 380 | | | | | |
| AGA | GTG | GAA | GCC | ATG | CTC | AAT | GAC | CGC | CGC | CGC | CTG | GCC | CTG | GAG | AAC | 1200 |
| Arg | Val | Glu | Ala | Met | Leu | Asn | Asp | Arg | Arg | Arg | Leu | Ala | Leu | Glu | Asn | |
| 385 | | | | | 390 | | | | | 395 | | | | | 400 | |
| TAC | ATC | ACC | GCT | CTG | CAG | GCT | GTT | CCT | CCT | CGG | CCT | CGT | CAC | GTG | TTC | 1248 |
| Tyr | Ile | Thr | Ala | Leu | Gln | Ala | Val | Pro | Pro | Arg | Pro | Arg | His | Val | Phe | |
| | | | | 405 | | | | | 410 | | | | | 415 | | |
| AAT | ATG | CTA | AAG | AAG | TAT | GTC | CGC | GCA | GAA | CAG | AAG | GAC | AGA | CAG | CAC | 1296 |
| Asn | Met | Leu | Lys | Lys | Tyr | Val | Arg | Ala | Glu | Gln | Lys | Asp | Arg | Gln | His | |
| | | | | 420 | | | | | 425 | | | | | 430 | | |
| ACC | CTG | AAG | CAT | TTC | GAG | CAT | GTG | CGC | ATG | GTG | GAT | CCC | AAG | AAA | GCC | 1344 |
| Thr | Leu | Lys | His | Phe | Glu | His | Val | Arg | Met | Val | Asp | Pro | Lys | Lys | Ala | |
| | | | 435 | | | | | 440 | | | | | 445 | | | |
| GCT | CAG | ATC | CGG | TCC | CAG | GTT | ATG | ACA | CAC | CTC | CGT | GTG | ATT | TAT | GAG | 1392 |
| Ala | Gln | Ile | Arg | Ser | Gln | Val | Met | Thr | His | Leu | Arg | Val | Ile | Tyr | Glu | |
| | 450 | | | | | 455 | | | | | 460 | | | | | |
| CGC | ATG | AAT | CAG | TCT | CTC | TCC | CTG | CTC | TAC | AAC | GTG | CCT | GCA | GTG | GCC | 1440 |
| Arg | Met | Asn | Gln | Ser | Leu | Ser | Leu | Leu | Tyr | Asn | Val | Pro | Ala | Val | Ala | |
| 465 | | | | | 470 | | | | | 475 | | | | | 480 | |
| GAG | GAG | ATT | CAG | GAT | GAA | GTT | GAT | GAG | CTG | CTT | CAG | AAA | GAG | CAA | AAC | 1488 |
| Glu | Glu | Ile | Gln | Asp | Glu | Val | Asp | Glu | Leu | Leu | Gln | Lys | Glu | Gln | Asn | |
| | | | | 485 | | | | | 490 | | | | | 495 | | |
| TAT | TCA | GAT | GAC | GTC | TTG | GCC | AAC | ATG | ATT | AGT | GAA | CCA | AGG | ATC | AGT | 1536 |
| Tyr | Ser | Asp | Asp | Val | Leu | Ala | Asn | Met | Ile | Ser | Glu | Pro | Arg | Ile | Ser | |
| | | | 500 | | | | | 505 | | | | | 510 | | | |
| TAC | GGA | AAC | GAT | GCT | CTC | ATG | CCA | TCT | TTG | ACC | GAA | ACG | AAA | ACC | ACC | 1584 |
| Tyr | Gly | Asn | Asp | Ala | Leu | Met | Pro | Ser | Leu | Thr | Glu | Thr | Lys | Thr | Thr | |
| | | 515 | | | | | 520 | | | | | 525 | | | | |
| GTG | GAG | CTC | CTT | CCC | GTG | AAT | GGA | GAG | TTC | AGC | CTG | GAC | GAT | CTC | CAG | 1632 |
| Val | Glu | Leu | Leu | Pro | Val | Asn | Gly | Glu | Phe | Ser | Leu | Asp | Asp | Leu | Gln | |
| | 530 | | | | | 535 | | | | | 540 | | | | | |
| CCG | TGG | CAT | TCT | TTT | GGG | GCT | GAC | TCT | GTG | CCA | GCC | AAC | ACA | GAA | AAC | 1680 |
| Pro | Trp | His | Ser | Phe | Gly | Ala | Asp | Ser | Val | Pro | Ala | Asn | Thr | Glu | Asn | |
| 545 | | | | | 550 | | | | | 555 | | | | | 560 | |

| | | | | | | | | | | | | | | | | |
|---|---|---|---|---|---|---|---|---|---|---|---|---|---|---|---|---|
| GAA | GTT | GAG | CCT | GTT | GAT | GCC | CGC | CCT | GCT | GCC | GAC | CGA | GGA | CTG | ACC | 1728 |
| Glu | Val | Glu | Pro | Val | Asp | Ala | Arg | Pro | Ala | Ala | Asp | Arg | Gly | Leu | Thr | |
| | | | 565 | | | | | 570 | | | | | 575 | | | |
| ACT | CGA | CCA | GGT | TCT | GGG | TTG | ACA | AAT | ATC | AAG | ACG | GAG | GAG | ATC | TCT | 1776 |
| Thr | Arg | Pro | Gly | Ser | Gly | Leu | Thr | Asn | Ile | Lys | Thr | Glu | Glu | Ile | Ser | |
| | | | 580 | | | | | 585 | | | | | 590 | | | |
| GAA | GTG | AAG | ATG | GAT | GCA | GAA | TTC | CGA | CAT | GAC | TCA | GGA | TAT | GAA | GTT | 1824 |
| Glu | Val | Lys | Met | Asp | Ala | Glu | Phe | Arg | His | Asp | Ser | Gly | Tyr | Glu | Val | |
| | | 595 | | | | | 600 | | | | | 605 | | | | |
| CAT | CAT | CAA | AAA | TTG | GTG | TTC | TTT | GCA | GAA | GAT | GTG | GGT | TCA | AAC | AAA | 1872 |
| His | His | Gln | Lys | Leu | Val | Phe | Phe | Ala | Glu | Asp | Val | Gly | Ser | Asn | Lys | |
| | 610 | | | | | 615 | | | | | 620 | | | | | |
| GGT | GCA | ATC | ATT | GGA | CTC | ATG | GTG | GGC | GGT | GTT | GTC | ATA | GCG | ACA | GTG | 1920 |
| Gly | Ala | Ile | Ile | Gly | Leu | Met | Val | Gly | Gly | Val | Val | Ile | Ala | Thr | Val | |
| 625 | | | | | 630 | | | | | 635 | | | | | 640 | |
| ATC | GTC | ATC | ACC | TTG | GTG | ATG | CTG | AAG | AAG | AAA | CAG | TAC | ACA | TCC | ATT | 1968 |
| Ile | Val | Ile | Thr | Leu | Val | Met | Leu | Lys | Lys | Lys | Gln | Tyr | Thr | Ser | Ile | |
| | | | | 645 | | | | | 650 | | | | | 655 | | |
| CAT | CAT | GGT | GTG | GTG | GAG | GTT | GAC | GCC | GCT | GTC | ACC | CCA | GAG | GAG | CGC | 2016 |
| His | His | Gly | Val | Val | Glu | Val | Asp | Ala | Ala | Val | Thr | Pro | Glu | Glu | Arg | |
| | | | 660 | | | | | 665 | | | | | 670 | | | |
| CAC | CTG | TCC | AAG | ATG | CAG | CAG | AAC | GGC | TAC | GAA | AAT | CCA | ACC | TAC | AAG | 2064 |
| His | Leu | Ser | Lys | Met | Gln | Gln | Asn | Gly | Tyr | Glu | Asn | Pro | Thr | Tyr | Lys | |
| | | 675 | | | | | 680 | | | | | 685 | | | | |
| TTC | TTT | GAG | CAG | ATG | CAG | AAC | | | | | | | | | | 2085 |
| Phe | Phe | Glu | Gln | Met | Gln | Asn | | | | | | | | | | |
| 690 | | | | | 695 | | | | | | | | | | | |

(2) INFORMATION FOR SEQ ID NO: 10:

(i) SEQUENCE CHARACTERISTICS:
        (A) LENGTH: 16
        (B) TYPE: amino acid
        (C) STRANDEDNESS:
        (D) TOPOLOGY: linear (xi) SEQUENCE DESCRIPTION: SEQ ID NO: 10:

Lys Leu Leu Leu Leu Gly Ala Gly Glu Ser Gly Lys Ser Thr Ile Val
1               5                   10                  15

(2) INFORMATION FOR SEQ ID NO: 11:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQ ID NO: 11:

Met Leu Pro Gly Leu Ala Leu Leu Leu Leu
1               5                   10

(2) INFORMATION FOR SEQ ID NO: 12:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQ ID NO: 12:

Asp Ala Glu Phe Arg His Asp Ser Gly Tyr
1               5                   10

( 2 ) INFORMATION FOR SEQ ID NO: 13:

( i ) SEQUENCE CHARACTERISTICS:
        ( A ) LENGTH: 19
        ( B ) TYPE: amino acid
        ( C ) STRANDEDNESS:
        ( D ) TOPOLOGY: linear ( x i ) SEQUENCE DESCRIPTION: SEQ ID NO: 13:

Met Gln Gln Asn Gly Tyr Glu Asn Pro Thr Tyr Lys Phe Phe Glu Gln
1                     5                       10                     15

Met Gln Asn ( 2 ) INFORMATION FOR SEQ ID NO: 14:

( i ) SEQUENCE CHARACTERISTICS:
        ( A ) LENGTH: 19
        ( B ) TYPE: amino acid
        ( C ) STRANDEDNESS:
        ( D ) TOPOLOGY: linear ( x i ) SEQUENCE DESCRIPTION: SEQ ID NO: 14:

His Gly Val Val Glu Val Asp Ala Ala Val Thr Pro Glu Glu Arg His
1                     5                       10                     15

Leu Ser Lys ( 2 ) INFORMATION FOR SEQ ID NO: 15:

( i ) SEQUENCE CHARACTERISTICS:
        ( A ) LENGTH: 18
        ( B ) TYPE: amino acid
        ( C ) STRANDEDNESS:
        ( D ) TOPOLOGY: linear ( x i ) SEQUENCE DESCRIPTION: SEQ ID NO: 15:

Gly Val Val Glu Val Asp Ala Ala Val Thr Pro Glu Glu Arg His Leu
1                     5                       10                     15

Ser Lys ( 2 ) INFORMATION FOR SEQ ID NO: 16:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 16:

His His Gly Val Val Glu Val Asp Ala Ala Val Thr Pro Glu Glu
1                     5                       10                     15

( 2 ) INFORMATION FOR SEQ ID NO: 17:

( i ) SEQUENCE CHARACTERISTICS:
        ( A ) LENGTH: 26
        ( B ) TYPE: amino acid
        ( C ) STRANDEDNESS:
        ( D ) TOPOLOGY: linear ( x i ) SEQUENCE DESCRIPTION: SEQ ID NO: 17:

Lys Gln Tyr Thr Ser Ile His His Gly Val Val Glu Val Asp Ala Ala
1                     5                       10                     15

Val Thr Pro Glu Glu Arg His Leu Ser Lys
                20                     25

( 2 ) INFORMATION FOR SEQ ID NO: 18:

( i ) SEQUENCE CHARACTERISTICS:
  ( A ) LENGTH: 30
  ( B ) TYPE: amino acid
  ( C ) STRANDEDNESS:
  ( D ) TOPOLOGY: linear ( x i ) SEQUENCE DESCRIPTION: SEQ ID NO: 18:

```
Thr Val Ile Val Ile Thr Leu Val Met Leu His His Gly Val Val Glu
 1               5                  10                  15

Val Asp Ala Ala Val Thr Pro Glu Glu Arg His Leu Ser Lys
            20                  25                  30
```

( 2 ) INFORMATION FOR SEQ ID NO: 19:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( x i ) SEQUENCE DESCRIPTION: SEQ ID NO: 19:

CCACGCAGGA TCACGGGATC CATGCTGCCC AGCTTG                36

( 2 ) INFORMATION FOR SEQ ID NO: 20:

( i ) SEQUENCE CHARACTERISTICS:
    ( A ) LENGTH: 6
    ( B ) TYPE: nucleic acid
    ( C ) STRANDEDNESS: single
    ( D ) TOPOLOGY: linear ( x i ) SEQUENCE DESCRIPTION: SEQ ID NO: 20:

GGATCC                                                  6

( 2 ) INFORMATION FOR SEQ ID NO: 21:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( x i ) SEQUENCE DESCRIPTION: SEQ ID NO: 21:

CAGTACACAT CCATCTGATG ACATCATGGC GTGGTG                 36

( 2 ) INFORMATION FOR SEQ ID NO: 22:

( i ) SEQUENCE CHARACTERISTICS:
    ( A ) LENGTH: 35
    ( B ) TYPE: nucleic acid
    ( C ) STRANDEDNESS: single
    ( D ) TOPOLOGY: linear ( x i ) SEQUENCE DESCRIPTION: SEQ ID NO: 22:

CGCCATCTCT CCAGTGATGA ATGCAGCAGA ACGGA                  35

( 2 ) INFORMATION FOR SEQ ID NO: 23:

( i ) SEQUENCE CHARACTERISTICS:
    ( A ) LENGTH: 656
    ( B ) TYPE: amino acid
    ( C ) STRANDEDNESS:
    ( D ) TOPOLOGY: linear ( x i ) SEQUENCE DESCRIPTION: SEQ ID NO: 23:

```
Met Leu Pro Gly Leu Ala Leu Leu Leu Leu Ala Ala Trp Thr Ala Arg
 1               5                  10                  15
```

```
Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Gly Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Cys Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Thr Glu Ser Val Glu Glu Val Val Arg
    275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
            325                 330                 335

Glu Trp Glu Glu Ala Glu Arg Gln Ala Lys Asn Leu Pro Lys Ala Asp
        340                 345                 350

Lys Lys Ala Val Ile Gln His Phe Gln Glu Lys Val Glu Ser Leu Glu
    355                 360                 365

Gln Glu Ala Ala Asn Glu Arg Gln Gln Leu Val Glu Thr His Met Ala
        370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
            405                 410                 415

Asn Met Leu Lys Lys Tyr Val Arg Ala Glu Gln Lys Asp Arg Gln His
        420                 425                 430

Thr Leu Lys His Phe Glu His Val Arg Met Val Asp Pro Lys Lys Ala
```

|     |     |     |     | 435 |     |     |     |     | 440 |     |     |     |     | 445 |     |
| --- | --- | --- | --- | --- | --- | --- | --- | --- | --- | --- | --- | --- | --- | --- | --- |
| Ala | Gln | Ile | Arg | Ser | Gln | Val | Met | Thr | His | Leu | Arg | Val | Ile | Tyr | Glu |
|     | 450 |     |     |     |     | 455 |     |     |     |     | 460 |     |     |     |     |
| Arg | Met | Asn | Gln | Ser | Leu | Ser | Leu | Leu | Tyr | Asn | Val | Pro | Ala | Val | Ala |
| 465 |     |     |     |     | 470 |     |     |     |     | 475 |     |     |     |     | 480 |
| Glu | Glu | Ile | Gln | Asp | Glu | Val | Asp | Glu | Leu | Leu | Gln | Lys | Glu | Gln | Asn |
|     |     |     |     | 485 |     |     |     |     | 490 |     |     |     |     | 495 |     |
| Tyr | Ser | Asp | Asp | Val | Leu | Ala | Asn | Met | Ile | Ser | Glu | Pro | Arg | Ile | Ser |
|     |     |     | 500 |     |     |     |     | 505 |     |     |     |     | 510 |     |     |
| Tyr | Gly | Asn | Asp | Ala | Leu | Met | Pro | Ser | Leu | Thr | Glu | Thr | Lys | Thr | Thr |
|     |     |     | 515 |     |     |     |     | 520 |     |     |     |     | 525 |     |     |
| Val | Glu | Leu | Leu | Pro | Val | Asn | Gly | Glu | Phe | Ser | Leu | Asp | Asp | Leu | Gln |
|     | 530 |     |     |     |     | 535 |     |     |     |     | 540 |     |     |     |     |
| Pro | Trp | His | Ser | Phe | Gly | Ala | Asp | Ser | Val | Pro | Ala | Asn | Thr | Glu | Asn |
| 545 |     |     |     |     | 550 |     |     |     |     | 555 |     |     |     |     | 560 |
| Glu | Val | Glu | Pro | Val | Asp | Ala | Arg | Pro | Ala | Ala | Asp | Arg | Gly | Leu | Thr |
|     |     |     |     | 565 |     |     |     |     | 570 |     |     |     |     | 575 |     |
| Thr | Arg | Pro | Gly | Ser | Gly | Leu | Thr | Asn | Ile | Lys | Thr | Glu | Glu | Ile | Ser |
|     |     |     | 580 |     |     |     |     | 585 |     |     |     |     | 590 |     |     |
| Glu | Val | Lys | Met | Asp | Ala | Glu | Phe | Arg | His | Asp | Ser | Gly | Tyr | Glu | Val |
|     |     | 595 |     |     |     |     | 600 |     |     |     |     | 605 |     |     |     |
| His | His | Gln | Lys | Leu | Val | Phe | Phe | Ala | Glu | Asp | Val | Gly | Ser | Asn | Lys |
|     | 610 |     |     |     |     | 615 |     |     |     |     | 620 |     |     |     |     |
| Gly | Ala | Ile | Ile | Gly | Leu | Met | Val | Gly | Gly | Val | Val | Ile | Ala | Thr | Val |
| 625 |     |     |     |     | 630 |     |     |     |     | 635 |     |     |     |     | 640 |
| Ile | Val | Ile | Thr | Leu | Val | Met | Leu | Lys | Lys | Lys | Gln | Tyr | Thr | Ser | Ile |
|     |     |     |     | 645 |     |     |     |     | 650 |     |     |     |     | 655 |     |

( 2 ) INFORMATION FOR SEQ ID NO: 24:

( i ) SEQUENCE CHARACTERISTICS:
        ( A ) LENGTH: 676
        ( B ) TYPE: amino acid
        ( C ) STRANDEDNESS:
        ( D ) TOPOLOGY: linear ( x i ) SEQUENCE DESCRIPTION: SEQ ID NO: 24:

| Met | Leu | Pro | Gly | Leu | Ala | Leu | Leu | Leu | Leu | Ala | Ala | Trp | Thr | Ala | Arg |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ala | Leu | Glu | Val | Pro | Thr | Asp | Gly | Asn | Ala | Gly | Leu | Leu | Ala | Glu | Pro |
|     |     |     | 20 |     |     |     |     | 25 |     |     |     |     | 30 |     |     |
| Gln | Ile | Ala | Met | Phe | Cys | Gly | Arg | Leu | Asn | Met | His | Met | Asn | Val | Gln |
|     |     |     | 35 |     |     |     |     | 40 |     |     |     |     | 45 |     |     |
| Asn | Gly | Lys | Trp | Asp | Ser | Asp | Pro | Ser | Gly | Thr | Lys | Thr | Cys | Ile | Asp |
|     | 50 |     |     |     |     | 55 |     |     |     |     | 60 |     |     |     |     |
| Thr | Lys | Glu | Gly | Ile | Leu | Gln | Tyr | Cys | Gln | Glu | Val | Tyr | Pro | Gly | Leu |
| 65 |     |     |     |     | 70 |     |     |     |     | 75 |     |     |     |     | 80 |
| Gln | Ile | Thr | Asn | Val | Val | Glu | Ala | Asn | Gln | Pro | Val | Thr | Ile | Gln | Asn |
|     |     |     |     | 85 |     |     |     |     | 90 |     |     |     |     | 95 |     |
| Trp | Cys | Lys | Arg | Gly | Arg | Lys | Gln | Cys | Lys | Thr | His | Pro | His | Phe | Val |
|     |     |     | 100 |     |     |     |     | 105 |     |     |     |     | 110 |     |     |
| Ile | Pro | Tyr | Arg | Cys | Leu | Val | Gly | Glu | Phe | Val | Ser | Asp | Ala | Leu | Leu |
|     |     |     | 115 |     |     |     |     | 120 |     |     |     |     | 125 |     |     |
| Val | Pro | Asp | Lys | Cys | Lys | Phe | Leu | His | Gln | Glu | Arg | Met | Asp | Val | Cys |
|     |     | 130 |     |     |     |     | 135 |     |     |     |     | 140 |     |     |     |
| Glu | Thr | His | Leu | His | Trp | His | Thr | Val | Ala | Lys | Glu | Thr | Cys | Ser | Glu |

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Lys | Ser | Thr | Asn | Leu | His | Asp | Tyr | Gly | Met | Leu | Leu | Pro | Cys | Gly | Ile |
|     |     |     |     | 165 |     |     |     |     | 170 |     |     |     |     | 175 |     |
| Asp | Lys | Phe | Arg | Gly | Val | Glu | Phe | Val | Cys | Cys | Pro | Leu | Ala | Glu | Glu |
|     |     |     |     | 180 |     |     |     |     | 185 |     |     |     |     | 190 |     |
| Ser | Asp | Asn | Val | Asp | Ser | Ala | Asp | Ala | Glu | Glu | Asp | Asp | Cys | Asp | Val |
|     |     |     |     | 195 |     |     |     |     | 200 |     |     |     |     | 205 |     |
| Trp | Trp | Gly | Gly | Ala | Asp | Thr | Asp | Tyr | Ala | Asp | Gly | Ser | Glu | Asp | Lys |
|     |     |     |     | 210 |     |     |     |     | 215 |     |     |     |     | 220 |     |
| Val | Val | Glu | Val | Ala | Glu | Glu | Glu | Val | Ala | Glu | Val | Glu | Glu | Glu |     |
| 225 |     |     |     |     | 230 |     |     |     |     | 235 |     |     |     |     | 240 |
| Glu | Ala | Asp | Asp | Asp | Glu | Asp | Asp | Glu | Asp | Gly | Asp | Glu | Val | Glu | Glu |
|     |     |     |     | 245 |     |     |     |     | 250 |     |     |     |     | 255 |     |
| Glu | Ala | Glu | Glu | Pro | Tyr | Glu | Glu | Ala | Thr | Glu | Arg | Thr | Thr | Ser | Ile |
|     |     |     |     | 260 |     |     |     |     | 265 |     |     |     |     | 270 |     |
| Ala | Thr | Thr | Thr | Thr | Thr | Thr | Thr | Glu | Ser | Val | Glu | Glu | Val | Val | Arg |
|     |     |     |     | 275 |     |     |     |     | 280 |     |     |     |     | 285 |     |
| Val | Pro | Thr | Thr | Ala | Ala | Ser | Thr | Pro | Asp | Ala | Val | Asp | Lys | Tyr | Leu |
|     |     |     |     | 290 |     |     |     |     | 295 |     |     |     |     | 300 |     |
| Glu | Thr | Pro | Gly | Asp | Glu | Asn | Glu | His | Ala | His | Phe | Gln | Lys | Ala | Lys |
| 305 |     |     |     |     | 310 |     |     |     |     | 315 |     |     |     |     | 320 |
| Glu | Arg | Leu | Glu | Ala | Lys | His | Arg | Glu | Arg | Met | Ser | Gln | Val | Met | Arg |
|     |     |     |     | 325 |     |     |     |     | 330 |     |     |     |     | 335 |     |
| Glu | Trp | Glu | Glu | Ala | Glu | Arg | Gln | Ala | Lys | Asn | Leu | Pro | Lys | Ala | Asp |
|     |     |     |     | 340 |     |     |     |     | 345 |     |     |     |     | 350 |     |
| Lys | Lys | Ala | Val | Ile | Gln | His | Phe | Gln | Glu | Lys | Val | Glu | Ser | Leu | Glu |
|     |     |     |     | 355 |     |     |     |     | 360 |     |     |     |     | 365 |     |
| Gln | Glu | Ala | Ala | Asn | Glu | Arg | Gln | Gln | Leu | Val | Glu | Thr | His | Met | Ala |
|     | 370 |     |     |     |     | 375 |     |     |     |     | 380 |     |     |     |     |
| Arg | Val | Glu | Ala | Met | Leu | Asn | Asp | Arg | Arg | Arg | Leu | Ala | Leu | Glu | Asn |
| 385 |     |     |     |     | 390 |     |     |     |     | 395 |     |     |     |     | 400 |
| Tyr | Ile | Thr | Ala | Leu | Gln | Ala | Val | Pro | Pro | Arg | Pro | Arg | His | Val | Phe |
|     |     |     |     | 405 |     |     |     |     | 410 |     |     |     |     | 415 |     |
| Asn | Met | Leu | Lys | Lys | Tyr | Val | Arg | Ala | Glu | Gln | Lys | Asp | Arg | Gln | His |
|     |     |     |     | 420 |     |     |     |     | 425 |     |     |     |     | 430 |     |
| Thr | Leu | Lys | His | Phe | Glu | His | Val | Arg | Met | Val | Asp | Pro | Lys | Lys | Ala |
|     |     |     | 435 |     |     |     |     | 440 |     |     |     |     | 445 |     |     |
| Ala | Gln | Ile | Arg | Ser | Gln | Val | Met | Thr | His | Leu | Arg | Val | Ile | Tyr | Glu |
|     | 450 |     |     |     |     | 455 |     |     |     |     | 460 |     |     |     |     |
| Arg | Met | Asn | Gln | Ser | Leu | Ser | Leu | Leu | Tyr | Asn | Val | Pro | Ala | Val | Ala |
| 465 |     |     |     |     | 470 |     |     |     |     | 475 |     |     |     |     | 480 |
| Glu | Glu | Ile | Gln | Asp | Glu | Val | Asp | Glu | Leu | Leu | Gln | Lys | Glu | Gln | Asn |
|     |     |     |     | 485 |     |     |     |     | 490 |     |     |     |     | 495 |     |
| Tyr | Ser | Asp | Asp | Val | Leu | Ala | Asn | Met | Ile | Ser | Glu | Pro | Arg | Ile | Ser |
|     |     |     | 500 |     |     |     |     | 505 |     |     |     |     | 510 |     |     |
| Tyr | Gly | Asn | Asp | Ala | Leu | Met | Pro | Ser | Leu | Thr | Glu | Thr | Lys | Thr | Thr |
|     |     |     | 515 |     |     |     |     | 520 |     |     |     |     | 525 |     |     |
| Val | Glu | Leu | Leu | Pro | Val | Asn | Gly | Glu | Phe | Ser | Leu | Asp | Asp | Leu | Gln |
|     | 530 |     |     |     |     | 535 |     |     |     |     | 540 |     |     |     |     |
| Pro | Trp | His | Ser | Phe | Gly | Ala | Asp | Ser | Val | Pro | Ala | Asn | Thr | Glu | Asn |
| 545 |     |     |     |     | 550 |     |     |     |     | 555 |     |     |     |     | 560 |
| Glu | Val | Glu | Pro | Val | Asp | Ala | Arg | Pro | Ala | Ala | Asp | Arg | Gly | Leu | Thr |
|     |     |     |     | 565 |     |     |     |     | 570 |     |     |     |     | 575 |     |

```
Thr  Arg  Pro  Gly  Ser  Gly  Leu  Thr  Asn  Ile  Lys  Thr  Glu  Glu  Ile  Ser
               580                      585                      590

Glu  Val  Lys  Met  Asp  Ala  Glu  Phe  Arg  His  Asp  Ser  Gly  Tyr  Glu  Val
          595                      600                      605

His  His  Gln  Lys  Leu  Val  Phe  Phe  Ala  Glu  Asp  Val  Gly  Ser  Asn  Lys
     610                      615                      620

Gly  Ala  Ile  Ile  Gly  Leu  Met  Val  Gly  Gly  Val  Val  Ile  Ala  Thr  Val
625                      630                      635                      640

Ile  Val  Ile  Thr  Leu  Val  Met  Leu  Lys  Lys  Lys  Gln  Tyr  Thr  Ser  Ile
               645                      650                      655

His  His  Gly  Val  Val  Glu  Val  Asp  Ala  Ala  Val  Thr  Pro  Glu  Glu  Arg
          660                      665                      670

His  Leu  Ser  Lys
          675
```

( 2 ) INFORMATION FOR SEQ ID NO: 25:

( i ) SEQUENCE CHARACTERISTICS:
        ( A ) LENGTH: 58
        ( B ) TYPE: amino acid
        ( C ) STRANDEDNESS:
        ( D ) TOPOLOGY: linear ( x i ) SEQUENCE DESCRIPTION: SEQ ID NO: 25:

```
Ala  Asp  Ser  Val  Pro  Ala  Asn  Thr  Glu  Asn  Glu  Val  Glu  Pro  Val  Asp
1                   5                        10                      15

Ala  Arg  Pro  Ala  Ala  Asp  Arg  Gly  Leu  Thr  Thr  Arg  Pro  Gly  Ser  Gly
               20                        25                      30

Leu  Thr  Asn  Ile  Lys  Thr  Glu  Glu  Ile  Ser  Glu  Val  Lys  Met  Asp  Ala
               35                        40                      45

Glu  Phe  Arg  His  Asp  Ser  Gly  Tyr  Glu  Val
          50                        55
```

( 2 ) INFORMATION FOR SEQ ID NO: 26:

( i ) SEQUENCE CHARACTERISTICS:
        ( A ) LENGTH: 56
        ( B ) TYPE: amino acid
        ( C ) STRANDEDNESS:
        ( D ) TOPOLOGY: linear ( x i ) SEQUENCE DESCRIPTION: SEQ ID NO: 26:

```
Val  Ile  Val  Ile  Thr  Leu  Val  Met  Leu  Lys  Lys  Lys  Gln  Tyr  Thr  Ser
1                   5                        10                      15

Ile  His  His  Gly  Val  Val  Glu  Val  Asp  Ala  Ala  Val  Thr  Pro  Glu  Glu
               20                        25                      30

Arg  His  Leu  Ser  Lys  Met  Gln  Gln  Asn  Gly  Tyr  Glu  Asn  Pro  Thr  Tyr
               35                        40                      45

Lys  Phe  Phe  Glu  Gln  Met  Gln  Asn
          50                        55
```

( 2 ) INFORMATION FOR SEQ ID NO: 27:

( i ) SEQUENCE CHARACTERISTICS:
        ( A ) LENGTH: 695
        ( B ) TYPE: amino acid
        ( C ) STRANDEDNESS: single
        ( D ) TOPOLOGY: linear ( x i ) SEQUENCE DESCRIPTION: SEQ ID NO: 27:

```
Met  Leu  Pro  Gly  Leu  Ala  Leu  Leu  Leu  Leu  Ala  Ala  Trp  Thr  Ala  Arg
1                   5                        10                      15
```

```
Ala  Leu  Glu  Val  Pro  Thr  Asp  Gly  Asn  Ala  Gly  Leu  Leu  Ala  Glu  Pro
          20                      25                      30

Gln  Ile  Ala  Met  Phe  Cys  Gly  Arg  Leu  Asn  Met  His  Met  Asn  Val  Gln
               35                      40                 45

Asn  Gly  Lys  Trp  Asp  Ser  Asp  Pro  Ser  Gly  Thr  Lys  Thr  Cys  Ile  Asp
     50                      55                      60

Thr  Lys  Glu  Gly  Ile  Leu  Gln  Tyr  Cys  Gln  Glu  Val  Tyr  Pro  Gly  Leu
65                       70                      75                           80

Gln  Ile  Thr  Asn  Val  Val  Glu  Ala  Asn  Gln  Pro  Val  Thr  Ile  Gln  Asn
               85                      90                           95

Trp  Cys  Lys  Arg  Gly  Arg  Lys  Gln  Cys  Lys  Thr  His  Pro  His  Phe  Val
               100                     105                     110

Ile  Pro  Tyr  Arg  Cys  Leu  Val  Gly  Glu  Phe  Val  Ser  Asp  Ala  Leu  Leu
               115                     120                     125

Val  Pro  Asp  Lys  Cys  Lys  Phe  Leu  His  Gln  Glu  Arg  Met  Asp  Val  Cys
     130                     135                     140

Glu  Thr  His  Leu  His  Trp  His  Thr  Val  Ala  Lys  Glu  Thr  Cys  Ser  Glu
145                      150                     155                          160

Lys  Ser  Thr  Asn  Leu  His  Asp  Tyr  Gly  Met  Leu  Leu  Pro  Cys  Gly  Ile
               165                     170                     175

Asp  Lys  Phe  Arg  Gly  Val  Glu  Phe  Val  Cys  Cys  Pro  Leu  Ala  Glu  Glu
               180                     185                     190

Ser  Asp  Asn  Val  Asp  Ser  Ala  Asp  Ala  Glu  Glu  Asp  Asp  Cys  Asp  Val
          195                     200                     205

Trp  Trp  Gly  Gly  Ala  Asp  Thr  Asp  Tyr  Ala  Asp  Gly  Ser  Glu  Asp  Lys
     210                     215                     220

Val  Val  Glu  Val  Ala  Glu  Glu  Glu  Val  Ala  Glu  Val  Glu  Glu  Glu  Glu
225                      230                     235                          240

Glu  Ala  Asp  Asp  Asp  Glu  Asp  Asp  Glu  Asp  Gly  Asp  Glu  Val  Glu  Glu
                    245                     250                          255

Glu  Ala  Glu  Glu  Pro  Tyr  Glu  Glu  Ala  Thr  Glu  Arg  Thr  Thr  Ser  Ile
               260                     265                     270

Ala  Thr  Thr  Thr  Thr  Thr  Thr  Thr  Glu  Ser  Val  Glu  Glu  Val  Val  Arg
               275                     280                     285

Val  Pro  Thr  Thr  Ala  Ala  Ser  Thr  Pro  Asp  Ala  Val  Asp  Lys  Tyr  Leu
     290                     295                     300

Glu  Thr  Pro  Gly  Asp  Glu  Asn  Glu  His  Ala  His  Phe  Gln  Lys  Ala  Lys
305                      310                     315                          320

Glu  Arg  Leu  Glu  Ala  Lys  His  Arg  Glu  Arg  Met  Ser  Gln  Val  Met  Arg
               325                     330                     335

Glu  Trp  Glu  Glu  Ala  Glu  Arg  Gln  Ala  Lys  Asn  Leu  Pro  Lys  Ala  Asp
          340                     345                     350

Lys  Lys  Ala  Val  Ile  Gln  His  Phe  Gln  Glu  Lys  Val  Glu  Ser  Leu  Glu
               355                     360                     365

Gln  Glu  Ala  Ala  Asn  Glu  Arg  Gln  Gln  Leu  Val  Glu  Thr  His  Met  Ala
          370                     375                     380

Arg  Val  Glu  Ala  Met  Leu  Asn  Asp  Arg  Arg  Arg  Leu  Ala  Leu  Glu  Asn
385                      390                     395                          400

Tyr  Ile  Thr  Ala  Leu  Gln  Ala  Val  Pro  Pro  Arg  Pro  Arg  His  Val  Phe
               405                     410                     415

Asn  Met  Leu  Lys  Lys  Tyr  Val  Arg  Ala  Glu  Gln  Lys  Asp  Arg  Gln  His
               420                     425                     430

Thr  Leu  Lys  His  Phe  Glu  His  Val  Arg  Met  Val  Asp  Pro  Lys  Lys  Ala
```

|   | 435 |   |   |   | 440 |   |   |   | 445 |   |   |   |
|---|---|---|---|---|---|---|---|---|---|---|---|---|

Ala Gln Ile Arg Ser Gln Val Met Thr His Leu Arg Val Ile Tyr Glu
450                     455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
            485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
            595                 600                 605

His His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
690                 695

(2) INFORMATION FOR SEQ ID NO: 28:

(i) SEQUENCE CHARACTERISTICS:
        (A) LENGTH: 2274
        (B) TYPE: nucleic acid
        (C) STRANDEDNESS: double
        (D) TOPOLOGY: linear (xi) SEQUENCE DESCRIPTION: SEQ ID NO: 28:

GCTGTGGCAG GGAAGGGGCC ACC ATG GGA TGT ACG CTG AGC GCA GAG GAG   50
                                 Met Gly Cys Thr Leu Ser Ala Glu Glu
                                 1                 5

AGA GCC GCC CTC GAG CGG AGC AAG GCG ATT GAG AAA AAC CTC AAA GAA   98
Arg Ala Ala Leu Glu Arg Ser Lys Ala Ile Glu Lys Asn Leu Lys Glu
 10                  15                  20                  25

GAT GGC ATC AGC GCC GCC AAA GAC GTG AAA TTA CTC CTG CTG GGG GCT  146
Asp Gly Ile Ser Ala Ala Lys Asp Val Lys Leu Leu Leu Leu Gly Ala
             30                  35                  40

GGA GAA TCA GGA AAA AGC ACC ATT GTG AAG CAG ATG AAG ATC ATC CAT  194
Gly Glu Ser Gly Lys Ser Thr Ile Val Lys Gln Met Lys Ile Ile His
             45                  50                  55

GAA GAT GGC TTC TCT GGG GAA GAC GTG AAG CAG TAC AAG CCT GTG GTC  242
Glu Asp Gly Phe Ser Gly Glu Asp Val Lys Gln Tyr Lys Pro Val Val
         60                  65                  70

| | | | | | | | | | | | | | | | | |
|---|---|---|---|---|---|---|---|---|---|---|---|---|---|---|---|---|
| TAC | AGC | AAC | ACC | ATC | CAG | TCT | CTG | GCG | GCC | ATT | GTC | CGG | GCC | ATG | GAC | 290 |
| Tyr | Ser 75 | Asn | Thr | Ile | Gln | Ser 80 | Leu | Ala | Ala | Ile | Val 85 | Arg | Ala | Met | Asp | |
| ACT | TTG | GGC | GTG | GAG | TAT | GGT | GAC | AAG | GAG | AGG | AAG | ACG | GAC | TCC | AAG | 338 |
| Thr 90 | Leu | Gly | Val | Glu | Tyr 95 | Gly | Asp | Lys | Glu | Arg 100 | Lys | Thr | Asp | Ser | Lys 105 | |
| ATG | GTG | TGT | GAC | GTG | GTG | AGT | CGT | ATG | GAA | GAC | ACT | GAA | CCG | TTC | TCT | 386 |
| Met | Val | Cys | Asp | Val 110 | Val | Ser | Arg | Met | Glu 115 | Asp | Thr | Glu | Pro | Phe 120 | Ser | |
| GCA | GAA | CTT | CTT | TCT | GCC | ATG | ATG | CGA | CTC | TGG | GGC | GAC | TCG | GGG | ATC | 434 |
| Ala | Glu | Leu | Leu 125 | Ser | Ala | Met | Met | Arg 130 | Leu | Trp | Gly | Asp | Ser 135 | Gly | Ile | |
| CAG | GAG | TGC | TTC | AAC | CGA | TCT | CGG | GAG | TAT | CAG | CTC | AAT | GAC | TCT | GCC | 482 |
| Gln | Glu | Cys 140 | Phe | Asn | Arg | Ser | Arg 145 | Glu | Tyr | Gln | Leu | Asn 150 | Asp | Ser | Ala | |
| AAA | TAC | TAC | CTG | GAC | AGC | CTG | GAT | CGG | ATT | GGA | GCC | GGT | GAC | TAC | CAG | 530 |
| Lys | Tyr 155 | Tyr | Leu | Asp | Ser | Leu 160 | Asp | Arg | Ile | Gly | Ala 165 | Gly | Asp | Tyr | Gln | |
| CCC | ACT | GAG | CAG | GAC | ATC | CTC | CGA | ACC | AGA | GTC | AAA | ACA | ACT | GGC | ATC | 578 |
| Pro 170 | Thr | Glu | Gln | Asp | Ile 175 | Leu | Arg | Thr | Arg | Val 180 | Lys | Thr | Thr | Gly | Ile 185 | |
| GTA | GAA | ACC | CAC | TTC | ACC | TTC | AAG | AAC | CTC | CAC | TTC | AGG | CTG | TTT | GAC | 626 |
| Val | Glu | Thr | His | Phe 190 | Thr | Phe | Lys | Asn | Leu 195 | His | Phe | Arg | Leu | Phe 200 | Asp | |
| GTC | GGG | GGC | CAG | CGA | TCT | GAA | CGC | AAG | AAG | TGG | ATC | CAC | TGC | TTT | GAG | 674 |
| Val | Gly | Gly | Gln | Arg 205 | Ser | Glu | Arg | Lys | Lys 210 | Trp | Ile | His | Cys | Phe 215 | Glu | |
| GAT | GTC | ACG | GCC | ATC | ATC | TTC | TGT | GTC | GCA | CTC | AGC | GGC | TAT | GAC | CAG | 722 |
| Asp | Val | Thr 220 | Ala | Ile | Ile | Phe | Cys 225 | Val | Ala | Leu | Ser | Gly 230 | Tyr | Asp | Gln | |
| GTG | CTC | CAC | GAG | GAC | GAA | ACC | ACG | AAC | CGC | ATG | CAC | GAA | TCC | CTG | AAG | 770 |
| Val | Leu 235 | His | Glu | Asp | Glu | Thr 240 | Thr | Asn | Arg | Met | His 245 | Glu | Ser | Leu | Lys | |
| CTC | TTC | GAC | AGC | ATC | TGC | AAC | AAC | AAG | TGG | TTC | ACA | GAC | ACA | TCT | ATT | 818 |
| Leu 250 | Phe | Asp | Ser | Ile | Cys 255 | Asn | Asn | Lys | Trp | Phe 260 | Thr | Asp | Thr | Ser | Ile 265 | |
| ATC | CTG | TTT | CTC | AAC | AAG | AAG | GAC | ATA | TTT | GAG | GAG | AAG | ATC | AAG | AAG | 866 |
| Ile | Leu | Phe | Leu | Asn 270 | Lys | Lys | Asp | Ile | Phe 275 | Glu | Glu | Lys | Ile | Lys 280 | Lys | |
| TCC | CCA | CTC | ACC | ATC | TGC | TTT | CCT | GAA | TAC | ACA | CGC | CCC | AGT | GCC | TTC | 914 |
| Ser | Pro | Leu | Thr 285 | Ile | Cys | Phe | Pro | Glu 290 | Tyr | Thr | Gly | Pro | Ser 295 | Ala | Phe | |
| ACA | GAA | GCT | GTG | GCT | CAC | ATC | CAA | GGG | CAG | TAT | GAG | AGT | AAG | AAT | AAG | 962 |
| Thr | Glu | Ala 300 | Val | Ala | His | Ile | Gln 305 | Gly | Gln | Tyr | Glu | Ser 310 | Lys | Asn | Lys | |
| TCA | GCT | CAC | AAG | GAA | GTC | TAC | AGC | CAT | GTC | ACC | TGT | GCC | ACG | GAC | ACC | 1010 |
| Ser | Ala | His 315 | Lys | Glu | Val | Tyr | Ser 320 | His | Val | Thr | Cys | Ala 325 | Thr | Asp | Thr | |
| AAC | AAC | ATC | CAA | TTC | GTC | TTT | GAT | GCC | GTG | ACA | GAT | GTC | ATC | ATC | GCC | 1058 |
| Asn | Asn 330 | Ile | Gln | Phe | Val 335 | Phe | Asp | Ala | Val | Thr 340 | Asp | Val | Ile | Ile | Ala 345 | |
| AAA | AAC | CTA | CGG | GGC | TGT | GGA | CTC | TAC | TGAGCCCTGG | | | CCTCCTACCC | | | | 1105 |
| Lys | Asn | Leu | Arg 350 | Gly | Cys | Gly | Leu | Tyr | | | | | | | | |
| AGCCTGCCAC | TCACTCCTCC | CCTGGACCCA | GAGCTCTGTC | ACTGCTCAGA | TGCCCTGTTA | | | | | | | | | | | 1165 |
| ACTGAAGAAA | ACCTGGAGGC | TAGCCTTGGG | GGCAGGAGGA | GGCATCCTTT | GAGCATCCCC | | | | | | | | | | | 1225 |
| ACCCCACCCA | ACTTCAGCCT | CGTGACACGT | GGGAACAGGG | TTGGGCAGAG | GTGTGGAACA | | | | | | | | | | | 1285 |
| GCACAAGGCC | AGAGACCACG | GCATGCCACT | TGGGTGCTGC | TCACTGGTCA | GCTGTGTGTC | | | | | | | | | | | 1345 |

| | | | | | | |
|---|---|---|---|---|---|---|
| TTACACAGAG | GCCGAGTGGG | CAACACTGCC | ATCTGATTCA | GAATGGGCAT | GCCCTGTCCT | 1405 |
| CTGTACCTCT | TGTTCAGTGT | CCTGGTTTCT | CTTCCACCTT | GGTGATAGGA | TGGCTGGCAG | 1465 |
| GAAGGCCCCA | TGGAAGGTGC | TGCTTGATTA | GGGGATAGTC | GATGGCATCT | CTCAGCAGTC | 1525 |
| CTCAGGGTCT | GTTTGGTAGA | GGGTGGTTTC | GTCGACAAAA | GCCAACATGG | AATCAGGCCA | 1585 |
| CTTTTGGGGC | GCAAAGACTC | AGACTTTGGG | GACGGGTTCC | CTCCTCCTTC | ACTTTGGATC | 1645 |
| TTGGCCCCTC | TCTGGTCATC | TTCCCTTGCC | CTTGGGCTCC | CCAGGATACT | CAGCCCTGAC | 1705 |
| TCCCATGGGG | TTGGGAATAT | TCCTTAAGAC | TGGCTGACTG | CAAAGGTCAC | CGATGGAGAA | 1765 |
| ACATCCCTGT | GCTACAGAAT | TGGGGGTGGG | ACAGCTGAGG | GGGCAGGCGG | CTCTTTCCTG | 1825 |
| ATAGTTGATG | ACAAGCCCTG | AGAATGCCAT | CTGCTGGCTC | CACTCACACG | GGCTCAACTG | 1885 |
| TCCTGGGTGA | TAGTGACTTG | CCAGGCCACA | GGCTGCAGGT | CACAGACAGA | GCAGGCAAGC | 1945 |
| AGCCTTGCAA | CTGCAGATTA | CTTAGGAGA | AGCATCCTAG | CCCAGCTAA | CTTTGGACAG | 2005 |
| TCAGCATATG | TCCCTGCCAT | CCCTAGACAT | CTCCAGTCAG | CTGGTATCAC | AGCCAGTGGT | 2065 |
| TCAGACAGGT | TTGAATGCTC | ATGTGGCAGG | GGGCCCGGTA | CCCAGCTTTT | GTTCCCTTTA | 2125 |
| GTGAGGGTTA | ATTGCGCGCT | TGGGCTAATC | ATGGTCATAG | CTGTTGGGCG | TTGCTGGCGT | 2185 |
| TTTTCCATAG | GCTCCGCCCC | CTGACGAGAT | CACAAAAATC | GACGCTCAAG | TCAGAGGTGG | 2245 |
| CGAAACCGAC | AGACTATAAG | ATACCAGGC | | | | 2274 |

( 2 ) INFORMATION FOR SEQ ID NO: 29:

( i ) SEQUENCE CHARACTERISTICS:
        ( A ) LENGTH: 18
        ( B ) TYPE: amino acid
        ( C ) STRANDEDNESS:
        ( D ) TOPOLOGY: linear ( x i ) SEQUENCE DESCRIPTION: SEQ ID NO: 29:

Asp Val Gly Gly Gln Arg Ser Glu Arg Lys Lys Trp Ile His Cys Phe
 1               5                   10                  15
Glu Asp ( 2 ) INFORMATION FOR SEQ ID NO: 30:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( x i ) SEQUENCE DESCRIPTION: SEQ ID NO: 30:

Thr Ser Ile Ile Leu Phe Leu Asn Lys Lys Asp Leu
 1               5                   10

METHODS AND SYSTEMS FOR SCREENING POTENTIAL ALZHEIMER'S DISEASE THERAPEUTICS

This is a continuation of application Ser. No. 08/019,208, filed Feb. 18, 1993, now abandoned.

The field of the invention is Alzheimer's disease therapeutics.

BACKGROUND OF THE INVENTION

Alzheimer's disease (AD) is a progressive degenerative disorder of the brain that afflicts over four million people in the United States. No effective treatment is available. The most characteristic change observed upon post-mortem histopathological analysis of AD-afflicted brain tissue is the presence of neuritic and cerebrovascular plaques containing dense deposits of β-amyloid protein (Selkoe, Cell 58:611–612, 1989). β-amyloid is a 39–43 amino acid peptide (Glenner and Wong, biochem. biophys. Res. Commun. 120:885–890, 1984; Masters et al., Proc. Natl. Acad. Aci. USA 82:4345–4249, 1985) synthesized as part of a larger precursor protein referred to as amyloid precursor protein (APP), which is known to have a number of isoforms in humans ($APP_{695}$, Kang et al., Nature 325:733–736, 1987; $APP_{751}$, Ponte et al., Nature 331:525–527, 1988, and Tanzi et al., Nature 331:528–530, 1988; and $APP_{770}$, Kitaguchi et al., Nature 331:530–532, 1988). The amino terminal of β-amyloid is generated by cleavage of a peptide bond of APP which in $APP_{695}$ lies between Met596 and Asp597.

Although structural alterations of APP are implicated in the pathogenesis of Alzheimer's disease, it remains unknown how they cause the disease. No biological function for APP has been identified, although there is evidence that APP has a receptor-like architecture (Kang et al., Nature 325:733–736, 1987; Ponte et al., Nature 331:525–527, 1988; Tanzi et al., Nature 331:528–530, 1988; Kitaguchi et al., Nature 331:530–532, 1988), is located on the neuronal surface (Dyrks et al., EMBO J. 7:949–957, 1988), and possesses an evolutionarily conserved cytoplasmic domain (Yamada et al., Biochem. Biophys. Res. Commun. 149:665–671, 1987).

SUMMARY OF THE INVENTION

The methods and therapeutical compositions of the invention are based upon the discovery, described in detail below, that APP forms a complex with $G_o$, a major GTP-binding protein (or "G protein") in brain. Like all G proteins, a molecule of $G_o$ is made up of one α subunit and one βγ subunit. Two isoforms of $G_o$, known as $G_{o1}$ (or $G_{oA}$) and $G_{o2}$ (or $G_{oB}$), have been identified; they have slight amino acid differences in their α subunits, and are together referred to herein as $G_o$. The cDNA sequence and deduced amino acid sequence of the α subunits of each of $G_{o1}$ and $G_{o2}$ (as reported by Strathmann et al., Proc. Natl. Acad. Sci. USA 87:6477–6481, 1990) are shown in FIG. 4a (SEQ ID NO: 2) and FIG. 4b (SEQ ID NO: 28), respectively.

The finding that APP associates with $G_o$ is consistent with related findings concerning other G proteins, as disclosed in a second, commonly assigned application (U.S. Ser. No. 08/019,073) having the same inventor and filing date as the present application, which second application is herein incorporated by reference. The cytoplasmic $APP_{695}$ sequence $His^{657}$-$Lys^{676}$ (SEQ ID NO: 1) possesses a specific $G_o$-activating function, and is necessary for complex formation of this APP with $G_o$; this sequence, sometimes referred to as the "couplone" region of APP, is completely conserved in $APP_{751}$ and $APP_{770}$, as well as in mouse $APP_{695}$. This provides evidence that APP is a receptor coupled to $G_o$, and suggests that abnormal APP-$G_o$ signalling is involved in the Alzheimer's disease process.

The invention includes a method of identifying a therapeutic useful for treating or preventing Alzheimer's disease, which method includes the steps of contacting (a) a first molecule containing the couplone portion of APP (SEQ ID NO: 1) with (b) a second molecule containing the amino acid sequence of $G_o$ (SEQ ID NO: 2) or an APP-associating region of $G_o$ (SEQ ID NOs: 3, 4, or 5), in the presence of a candidate compound; and either (i) determining whether the candidate compound interferes with (i.e., inhibits partially or completely) the association of the first and second molecules, or (ii) determining whether the candidate compound interferes with the activation of the second molecule by the first molecule, such interference being an indication that the candidate compound is a potential therapeutic useful for treating or preventing Alzheimer's disease. The determining step may be accomplished by, for example, immmunoprecipitating the first molecule with an antibody specific for APP, and detecting the presence or amount of the second molecule which co-precipitates with the first molecule. Alternatively, the second molecule can be immunoprecipitated with an antibody specific for $G_o$, following which the presence or amount of the first molecule which co-precipitates with the second molecule is determined. Where activation is the criterion being measured, the determination step may be accomplished by contacting the second molecule with a substrate which is or includes GTP or an analog of GTP [such as GTPγS or Gpp(NH)p], and detecting or measuring the binding of the substrate to the second molecule, wherein such binding is evidence of activation of the second molecule by the first molecule. In preferred embodiments, the contacting step is carried out in a cell-free system; the $Mg^{2+}$ concentration at which the contacting step is carried out is between approximately $1'10^{-7}$ and $1\times10^{-2}M$, and the first molecule includes the cytoplasmic tail portion of $APP_{695}$ from residues 649 to 695 (SEQ ID NO: 6) and/or the membrane-spanning portion of $APP_{695}$ from residues 639 to 648 (SEQ ID NO: 7) (the entire membrane-spanning segment of $APP_{695}$ being from residues 625 to 648, SEQ ID NO: 8); the first molecule more preferably includes substantially all of APP (SEQ ID NO: 9). (Alternatively, the corresponding functional regions of $APP_{751}$ or $APP_{770}$, or any other APP, may be used.) The second molecule preferably contains two or three of the putative APP-associating regions referred to above, and may also contain one or more of the GTP-binding regions of $G_o$, corresponding to residues 35 to 50 (SEQ ID NO: 10), residues 201 to 218 (SEQ ID NO: 29), or residues 263 to 274 (SEQ ID NO: 30) of $G_{o1}$ [Kaziro, "Structure of the genes coding for the α subunits of G proteins", Ch. 1 in ADP-ribosylating Toxins and G proteins (Moss, J., and Vaughan, M. eds.) pp189–206, American society for Microbiology, Washington, D.C. (1988)], and more preferably contains substantially all of $G_o$ (SEQ ID NO: 2).

The invention also includes a system (e.g., a cell-free in vitro system) for screening candidate Alzheimer's disease therapeutics, which system includes a first polypeptide containing a sequence essentially identical to that of peptide 20 (SEQ ID NO: 1), and a second polypeptide containing a sequence essentially identical to one, two or three of the putative APP-associating regions of $G_o$ (SEQ ID NOs: 3, 4, and 5); the system may also include a means for detecting either (a) the association of the first polypeptide with the second polypeptide, or (b) the activation of the second polypeptide by the first polypeptide. The first polypeptide may conveniently be anchored to a solid material (e.g., a cellular membrane, a polystyrene surface, or a standard matrix material), or may be in a phospholipid vesicle. It may include a sequence essentially identical to the membrane-spanning region of APP, and/or a sequence essentially identical to the entire cytoplasmic tail of APP. The second molecule preferably contains the GTP-binding domain of $G_o$, and more preferably contains the entire sequence of $G_o$.

The invention also features a method for diminishing the activation of $G_o$ in a neuronal cell by treating the cell with a compound, such as a peptide fragment of $G_o$ or of the cytoplasmic tail of APP, which blocks association of neuronal $G_o$ with, and/or activation of neuronal $G_o$ by, the cytoplasmic tail of APP. The cell may be so treated in vivo (i.e., in an animal, e.g. a mammal such as a human or other primate, cow, horse, pig, sheep, goat, dog, cat, rat, mouse, guinea pig, hamster, or rabbit) or in vitro. This method may be used to prevent or treat the symptoms of Alzheimer's disease in a patient. Such a compound may include, for example, a peptide having fewer than 50 amino acids (preferably 40 or fewer, and more preferably 30 or fewer), and containing the sequence of peptide 20. Also within the invention is a DNA molecule (e.g., a plasmid or viral DNA) encoding such a peptide, and a therapeutic composition containing, in a pharmaceutically acceptable carrier, either the peptide or the DNA molecule.

In another aspect, the invention features a method for identifying a ligand for which APP is a receptor, which method includes the steps of providing an APP molecule, the cytoplasmic tail of which is accessible to a molecule of $G_o$;

contacting a candidate compound with the extracellular domain of the APP molecule; and detecting either (a) association of $G_o$ with the APP molecule, (b) dissociation of $G_o$ from the APP molecule, or (c) activation of $G_o$ by the APP molecule, such association, dissociation, or activation being evidence that the candidate compound is a ligand of APP.

Other features and advantages of the invention will be apparent from the detailed description set forth below, and from the claims.

BRIEF DESCRIPTION OF THE DRAWINGS

FIG. 4a is the cDNA sequence and deduced amino acid sequence of $G_{o1}\alpha$ (Strathmann et al., Proc. Natl. Acad. Sci. USA 87:6477–6481, 1990) (SEQ ID NO: 2).

FIG. 4b is the cDNA sequence and deduced amino acid sequence of $G_{o2}\alpha$ (Strathmann et al.) (SEQ ID NO: 28).

DETAILED DESCRIPTION

Figure 1A:
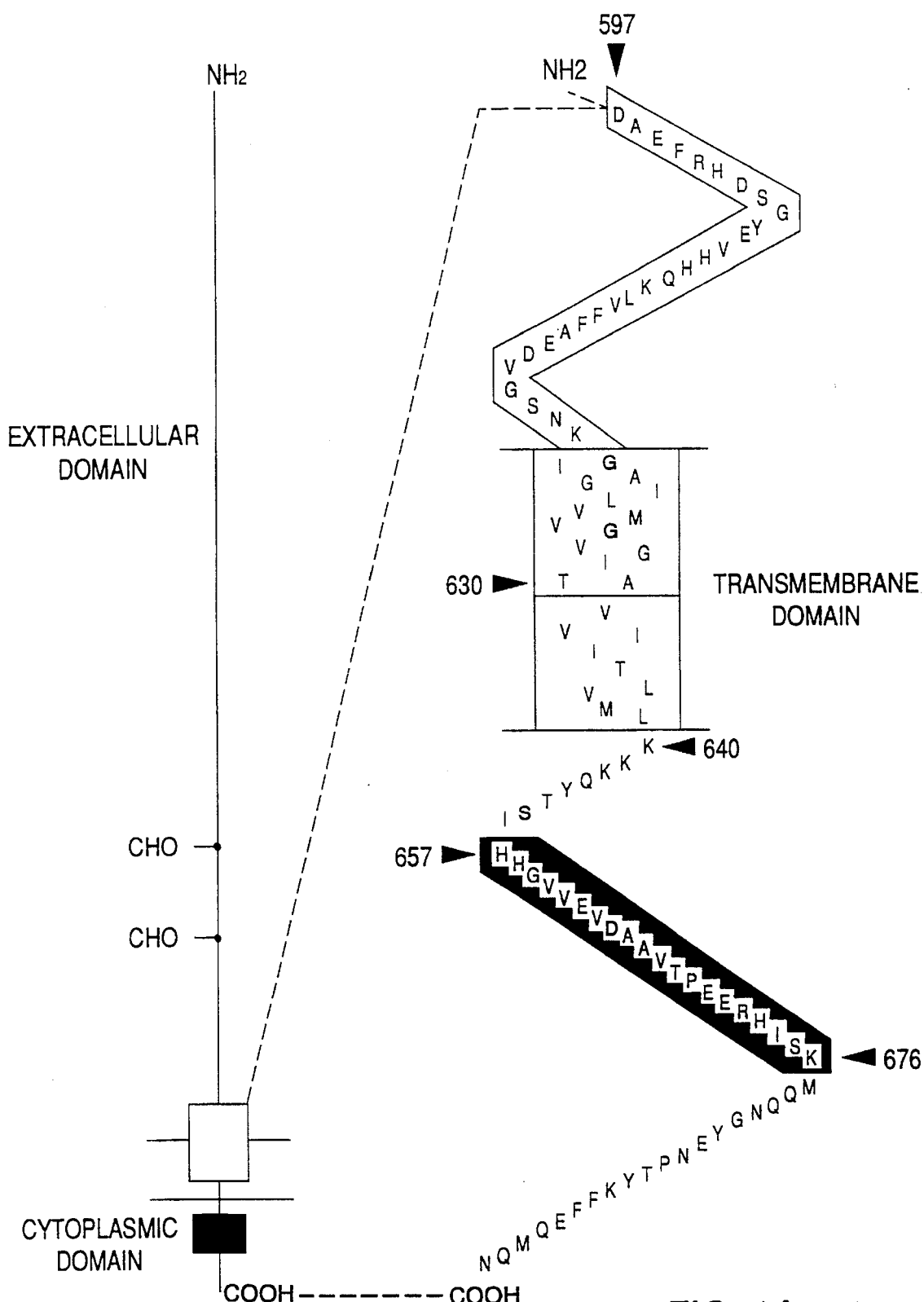
FIG. 1(a) is a schematic diagram illustrating the structural organization of APP. The hatched box contains the sequence of the β/A₄ protein; the black box contains the so-called "Peptide 20" or couplone sequence; filled circles are N-glycosylation sites. The numbers designate amino acid sequence numbers corresponding to $APP_{695}$.

It was previously shown that the insulin-like growth factor II receptor (IGF-IIR) couples directly to the G protein referred to as $G_i$ (Nishimoto et al., J. Biol. Chem. 264: 14029–14038, 1989) via a 14-residue section of the cytoplasmic tail of IGF-IIR, $Arg^{241}$-$Lys^{2423}$ (Okamoto et al., Cell 62:709–717, 1990; Okamoto et al., Proc. Natl. Acad. Sci. U.S.A. 88:8020–8023, 1991). The structural determinants for the $G_i$-activating function in IGF-IIR were defined as (i) two basic residues at the N-terminal region of the amino acid sequence, and (ii) a C-terminal motif of B—B—X—B or B—B—X—X—B (where B is a basic residue and X is a non-basic residue) (Okamoto et al., Cell 62:709–717, 1990). To assess whether APP might function as a G protein-coupled receptor, the amino acid sequence of human APP695 was examined for regions of less than 26 residues which satisfy (i) and (ii). The sequence $His^{657}$-$Lys^{676}$ is the only such region in the cytoplasmic domain of APP695. In two other isoforms of APP, APP751 (Ponte et al., Nature 331:525–527, 1988; Tanzi et al., Nature 331:528–530, 1988) and APP770 (Kitaguchi et al., Nature 331:530–532, 1988), as well as in mouse APP695 (Yamada et al., Biochem. Biophys. Res. Commun. 149:665–671, 1987), this sequence is completely conserved.

Preparation of peptides

A peptide corresponding to the $His^{657}$-$Lys^{676}$ region of APP [HHGVVEVDAAVTPEERHLSK (SEQ ID NO: 1)] was synthesized and purified by standard methods using solid phase synthesis; this peptide is referred to as "peptide 20". Similarly prepared were peptides corresponding to other regions of $APP_{695}$: APP(1–10), MLPGLALLLL (SEQ ID NO: 11); APP(597–606), DAEFRHDSGY (SEQ ID NO: 12); APP(677–695), MQQNGYENPTYKFFEQMQN (SEQ ID NO: 13); and APP(639–648), TVIVITLVML (SEQ ID NO: 7), a portion of the transmembrane region of APP; as well as the following variants of peptide 20: HGVVEVDAAVTPEERHLSK (H-deleted, SEQ ID NO: 14); GVVEVDAAVTPEERHLSK (HH-deleted, SEQ ID NO: 15); HHGVVEVDAAVTPEE (RHLSK-deleted, SEQ ID NO: 16); KQYTSIHHGVVEVDAAVTPEERHLSK (KQYTSI-added, SEQ ID NO: 17); and TVIVITLVMLH-HGVVEVDAAVTPEERHLSK (transmembrane region-connected peptide 20; SEQ ID NO: 18). Peptides were purified by HPLC to greater than 95% purity, and were used immediately after synthesis.

Materials and Methods.

Trimeric $G_o$ was purified to homogeneity from bovine brain as described (Katada et al., FEBS Lett. 213:353–358, 1987). This $G_o$ preparation was stored in 20 mM Hepes/NaOH (pH 7.4), 1 mM EDTA, and 0.7% CHAPS, and diluted $\geq$10 fold for assays. $G_{i3\alpha}$, which was used in combination with 1.5-fold concentrated G$\beta\gamma$ (Okamoto et al., Natl. Acad. Sci. U.S.A. 88:8020–8023, 1991), was prepared as described by Morishita et al., Biochim. Biophys. Acta 161:1280–1285, 1989. Low molecular weight G proteins were prepared as described by Matsui et al., J. Biol. Chem. 263:11071–4, 1988; G$\beta\gamma$ was purified from bovine brain as set forth in Katada et al., FEBS Lett. 213:353–358, 1987.

GTP$\gamma$S binding to $G_o$ was assayed in a buffer containing 50 mM Hepes/NaOH (pH 7.4), 100 $\mu$M EDTA, 120 $\mu$M MgCl$_2$, and 60 nM [$^{35}$S]GTP$\gamma$S (DuPont-New England Nuclear) at 37° C., and the fraction of total $G_o$ bound to GTP$\gamma$S was measured as described (Okamoto et al., Cell 62:709–717, 1990). GTP$\gamma$S binding to peptides was negligible. The total amount of $G_o$ in a given preparation was defined as the saturation amount of GTP$\gamma$S bound to $G_o$ following a 30-min incubation of $G_o$ with 10 mM Mg$^{2+}$ and $\geq$60 nM GTP$\gamma$S at 30° C.

Reconstitution of $G_o$ into phospholipid vesicles was accomplished with 1 mg/ml of phosphatidylcholine, using the gel filtration method (Nishimoto et al., J. Biol. Chem. 264:14029–14038, 1989). In a final incubation for GTP$\gamma$S binding, 5 nM of reconstituted $G_o$ was used.

For experiments exploring the effect of Mg$^{2+}$, the Mg$^{2+}$ concentration was set by using Mg-EDTA buffer (Birnbaumer et al., J. Eur. J. Biochem. 136:107–112, 1983).

Bovine brain membranes, prepared as described (Katada et al., FEBS Lett. 213:353–358, 1987) and suspended in buffer A [10 mM Hepes/NaOH (pH 7.4), 1 mM EDTA, 10 mM acetic acid, and 250 mM sucrose, plus a mixture (termed "PAL") of 2 mM PMSF, 20 $\mu$g/ml aprotinin, and 20 $\mu$M leupeptin], were centrifuged and the pellet was solubilized for 1 h at 4° C. in buffer B (10 mM Hepes/NaOH (ph 7.4), 1 mM EDTA, 120 mM NaCl, 0.5% CHAPS, and PAL). Following centrifugation of the material at 15000 rpm for 1 h, the supernatant (500 $\mu$g protein, unless specified) was incubated in buffer C (20 mM Hepes/NaOH (pH 7.4), 1 mM EDTA, 120 mM NaCl, and PAL) and 2% BSA with 22C11-coated protein G-Sepharose, which had been prepared by incubating protein G-Sepharose (Pharmacia) with anti-APP monoclonal antibody 22C11 (Boehringer Mannheim) for 1 h at 4° C. An antibody concentration of $\geq$2 $\mu$g/ml was found to saturate precipitation of APP and $G_o$, so 2 $\mu$g/ml was the concentration used for immunoprecipitation studies. As a control, 2 $\mu$g/ml of rabbit IgG was used. After overnight shaking at 4° C., the immunoprecipitated sample was centrifuged at 5000 rpm for 5 min. The pellet was washed three times with ice-cold buffer C and the final pellet was applied to SDS-PAGE. Electroblotting onto a PVDF sheet was performed as described (Okamoto et al., J. Biol. Chem. 266:1085–1091, 1991). After blocking with PBS containing 2% skim milk and 1% BSA, the sheet was incubated with the first antibody [1 $\mu$g/ml of 22C11; 1/1000 dilution of anti-$G_o\alpha$ monoclonal antibody GC/2 (DuPont-New England Nuclear); 1/1000 dilution of 1C1, a monoclonal antibody against the C-terminal peptide $_{677-695}$ of APP$_{695}$] for 4 h, and then exposed to horseradish peroxidase-conjugated goat IgG reactive for mouse or rabbit immunoglobulins for 2–4 h at room temperature. The antigenic bands were detected with an ECL detection kit (Amersham). YL1/2 (SERA Lab), an anti-tubulin antibody, was used at 1:500 dilution for immunodetection.

Effects of synthetic APP peptides on G proteins.

Figure 1B:
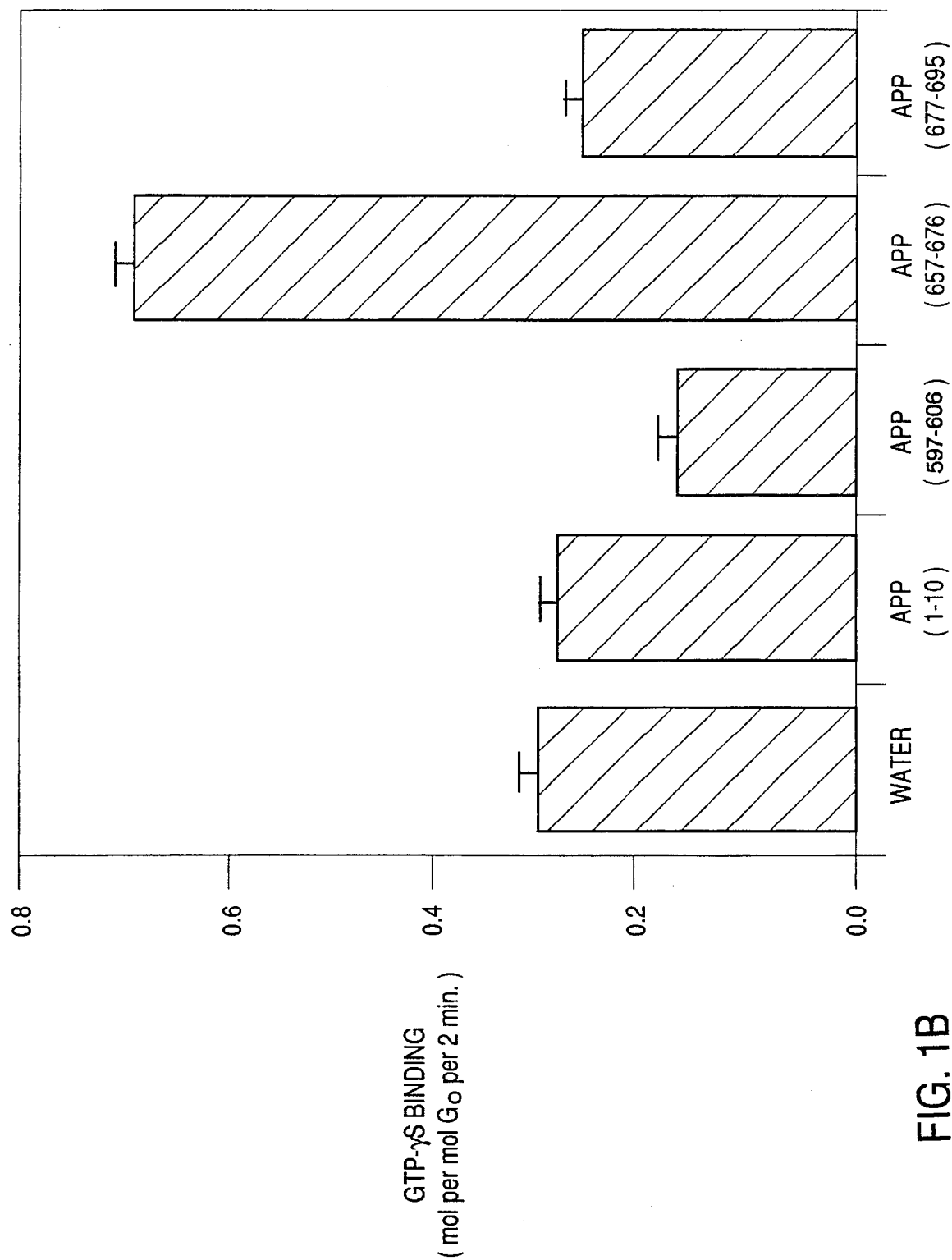
FIG. 1(b) is a bar graph illustrating the effects of synthetic APP peptides on $G_o$. In (b), (d), (e) and (f), values represent the mean ±S.E. of three experiments.
Figure 1C:
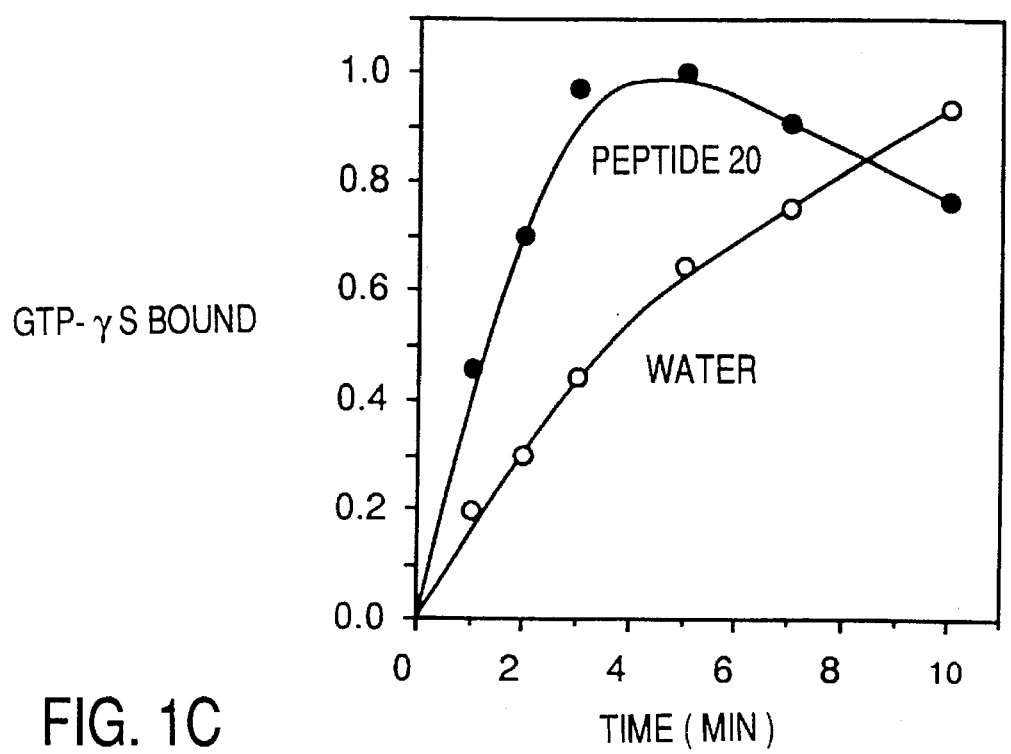
FIG. 1(c) is a graph illustrating the time course of the action of peptide 20 on $G_o$. Values represent the mean of three experiments. Since the S.E. was <5% of each value in this figure, the error bars are not indicated.

In the experiment shown in FIG. 1(b), 10 nM $G_o$ was incubated with water or 100 $\mu$M of each peptide for 2 min, and the amount of GTP$\gamma$S bound to $G_o$ at the end of this period was measured. In the experiment shown in FIG. 1(c), 10nM $G_o$ was incubated with water (O) or 100 $\mu$M peptide 20 (SEQ ID NO: 1) (●), and GTP$\gamma$S binding was measured at the indicated times. From FIG. 1(d), it can be seen that peptide 20 (SEQ ID NO: 1) stimulated the rate constant of GTP$\gamma$S binding to $G_o$ in a dose-dependent manner, whereas FIG. 1(b) shows that peptides from other regions of APP695 were ineffective. GTP$\gamma$S binding to $G_o$ in the presence or absence of peptide 20 (SEQ ID NO: 1) obeyed first-order kinetics according to the equation $$ln[(Bt-B)/BT]=-k_{app}t$$

(B is the binding at time t; BT is the total binding observable at infinite time; and $k_{app}$ is the rate constant for GTP$\gamma$S binding). The ability of peptide 20 (SEQ ID NO: 1) to activate $G_o$ was gradually decreased during storage at either −4° C. or −20° C.

Figure 1D:
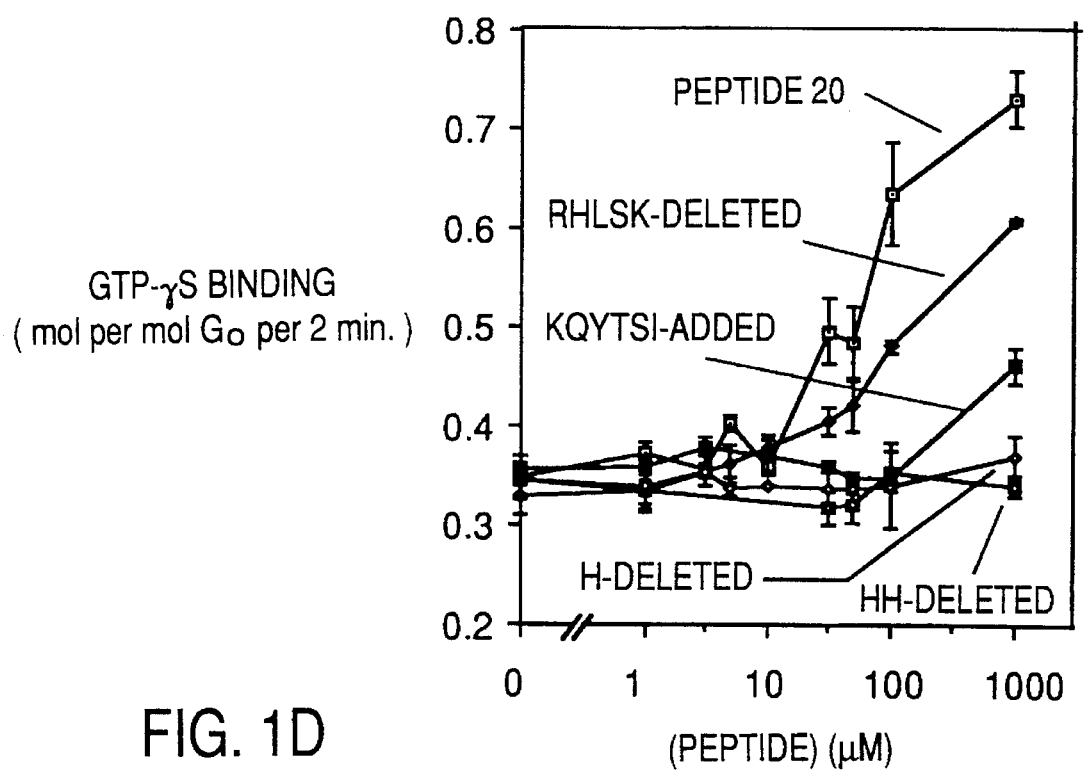
FIG. 1(d) is a graph illustrating the effects of peptide 20 variants on $G_o$.

Studies using structural variant peptides suggest that both the N-terminal basic residues and the C-terminal B—B—X—X—B motif play essential roles in the $G_o$-activating function of peptide 20 (SEQ ID NO: 1) [FIG. 1(d)]. In this experiment, 10 nM $G_o$ was incubated with various concentrations of HHGVVEVDAAVTPEERHLSK (peptide 20, SEQ ID NO: 1; □), HGVVEVDAAVTPEERHLSK (H-deleted, SEQ ID NO: 14; ◇), GVVEVDAAVTPEERHLSK (HH-deleted, SEQ ID NO: 15; □), HHGVVEVDAAVTPEE (RHLSK-deleted, SEQ ID NO: 16; ♦), or KQYTSIHH-GVVEVDAAVTPEERHLSK (KQYTSI-added, SEQ ID NO: 17; ■), and GTP$\gamma$S binding to $G_o$ at 2 min. was measured. FIG. 1(d) indicates which aspects of primary structure determine the $G_o$-activator function of peptide 20 (SEQ ID NO: 1). Deletion of either one or both of the N-terminal His residues nullified $G_o$-activator function of the peptide. The peptide (SEQ ID NO: 16) in which the C-terminal five residues of peptide 20 (SEQ ID NO: 1) has been deleted is several times less potent than peptide 20 (SEQ ID NO: 1).

Figure 1E:
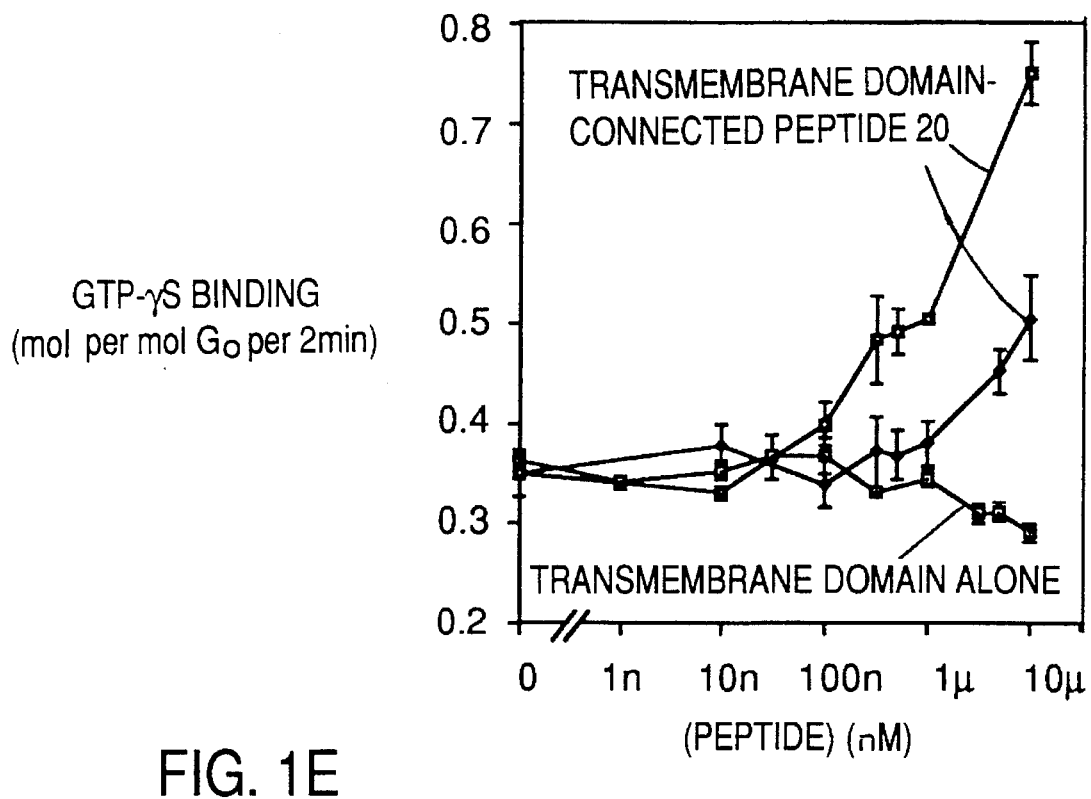
FIG. 1(e) is a graph illustrating the effect linkage with a transmembrane region has on the action of peptide 20 on $G_o$.

As illustrated in FIG. 1(e), $G_o$ reconstituted in phospholipid vesicles was incubated with transmembrane region-connected peptide 20 (TVIVITLVMLHHGVVEVDAAVT-PEERHLSK, SEQ ID NO: 18; □) or the partial sequence of the APP transmembrane domain alone (TVIVITLVML, SEQ ID NO: 7; □). Transmembrane region-connected peptide 20 (SEQ ID NO: 18) was also incubated with $G_o$ in the absence of phospholipids and the presence of 0.07% CHAPS (♦). The transmembrane region-connected peptide 20 (SEQ ID NO: 18) stimulated $G_o$ reconstituted in phospholipid vesicles with a potency 10 times greater than that of peptide 20 (SEQ ID NO: 1). The transmembrane region alone (SEQ ID NO: 7) was without effect on $G_o$. In the absence of phospholipids, transmembrane region-connected peptide 20 (SEQ ID NO: 18) showed an effect on $G_o$ no more potent than peptide 20 (SEQ ID NO: 1). Therefore, the stimulatory action of this transmembrane region-connected peptide (SEQ ID NO: 18) is attributed to the peptide 20 (SEQ ID NO: 1) sequence; the potentiating effect of the transmembrane region may be exerted by interactions with phospholipids.

Figure 1F:
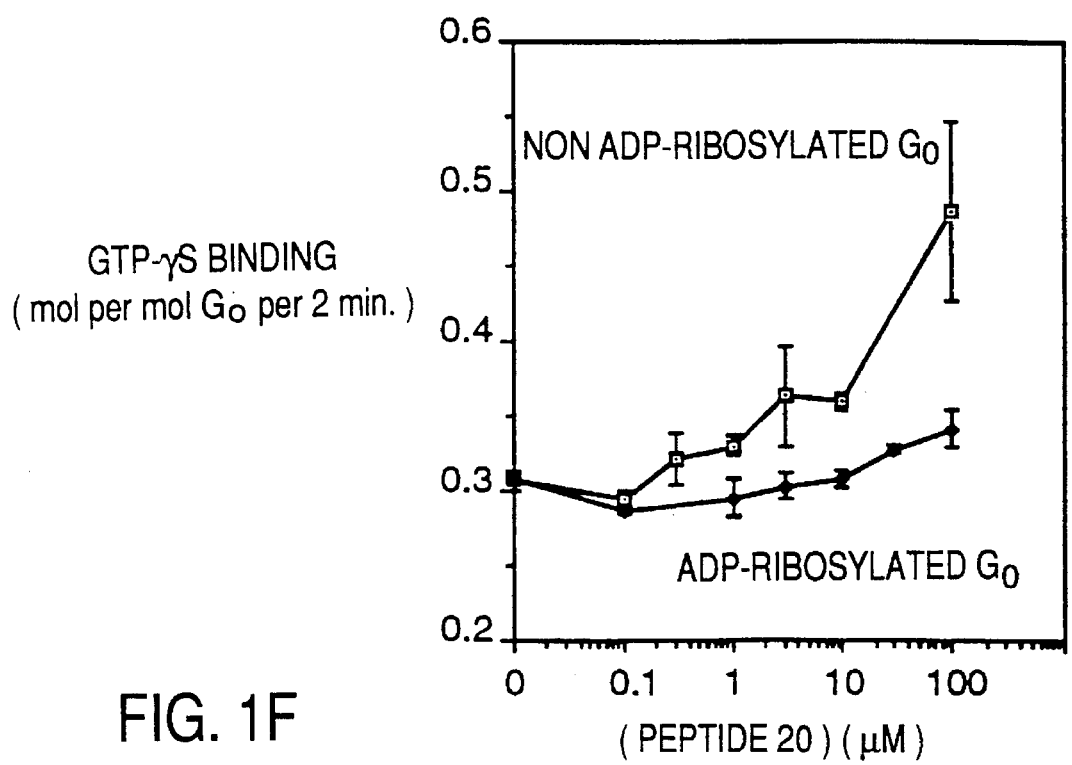
FIG. 1(f) is a graph illustrating the effect of pertussis toxin on peptide 20-induced stimulation of GTP-γS binding to $G_o$.

In the experiment shown in FIG. 1(f), ADP-ribosylation of $G_o$ was accomplished by incubating $G_o$ reconstituted in phospholipid vesicles with 10 µg/ml preactivated pertussis toxin in the presence of 10 µM NAD for 15 min at 30° C. as described (Okamoto et al., Cell 62:709–717, 1990). Preactivation of pertussis toxin (Funakoshi, Japan) was carried out by treating the toxin with 100 µM ATP and 1 mM DTT for 10 min at 30° C. Reconstitution of $G_o$ into phospholipid vesicles was accomplished with 1 mg/ml phosphatidylcholine (Sigman, P-5638) at a final $G_o$ concentration of 50.2 nM in a buffer containing 20 mM Hepes/NaOH (pH 7.4), 0.1 mM EDTA, 1 mM DTT, and 100 mM NaCl by the gel filtration method (Nishimoto et al., J. Biol. Chem. 264:14029–14038, 1989). In a final incubation for GTPγS binding, 5 nM of reconstituted $G_o$ was used. Increasing concentrations of peptide 20 (SEQ ID NO: 1) were incubated for 2 min with $G_o$ reconstituted in phospholipid vesicles which had been treated with pertussis toxin in the presence (♦) or absence (□) of NAD, and GTPγS binding to $G_o$ was measured.

Although peptide 20 (SEQ ID NO: 1) produced 2–3 fold stimulation of GTPγS binding to $G_o$ in the mid-range of $Mg^{2+}$ concentrations, the effect of peptide 20 (SEQ ID NO: 1) could not be observed at low ($\leq 100$ nM) or high ($\geq 10$ mM) $Mg^{2+}$ concentrations.

Peptide 20 (SEQ ID NO: 1) had little effect on G proteins other than $G_o$: $G_{i1}$, $G_{i2}$, $G_{i3}$, $G_S$, c-Ki-ras p21 and smg p25A were not stimulated by this peptide (data not shown). Thus, peptide 20 (SEQ ID NO: 1) activates $G_o$ in a receptor-like manner, suggesting that APP interacts directly with $G_o$ through the peptide 20 (SEQ ID NO: 1) region.

Coprecipitation of APP and $G_o$

Figure 2B:
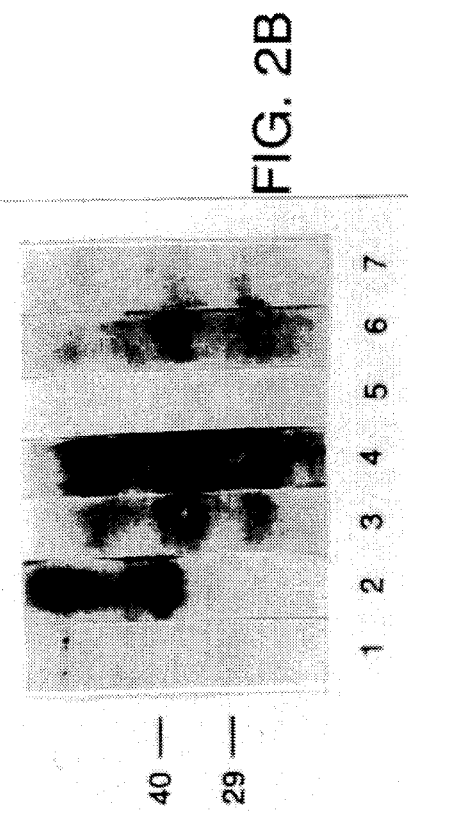
FIGS. 2a–2d is a set of SDS-PAGE gels analyzed by immunoblotting, which illustrate the immunoprecipitation of APP and $G_o$ by an anti-APP antibody from brain membranes. (2a) Immunoprecipitation of APP by 22C11. (2b) Immunoprecipitation of $G_o$ by 22C11. (2c) Effect of $Mg^{2+}$ on the immunoprecipitation of $G_o$ by 22C11. (2d) Effect of peptide 20 on 22C11-induced precipitation of $G_{o\alpha}$ (left) and APP (right). Each of the results presented in this figure was reproduced at least three times.
Figure 2D:
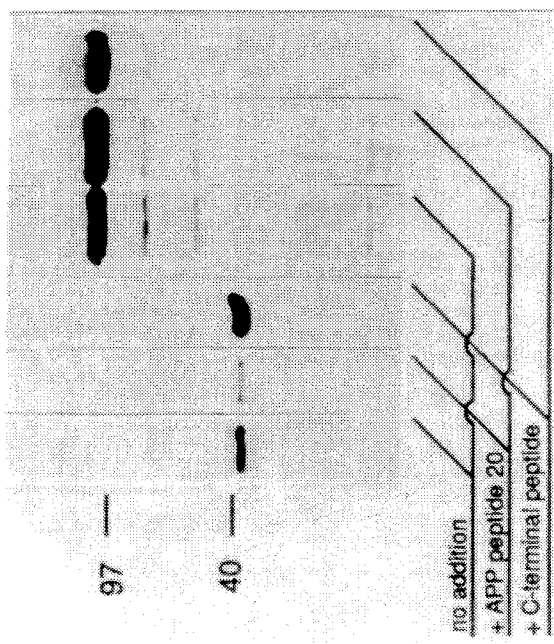
Figure 2A:
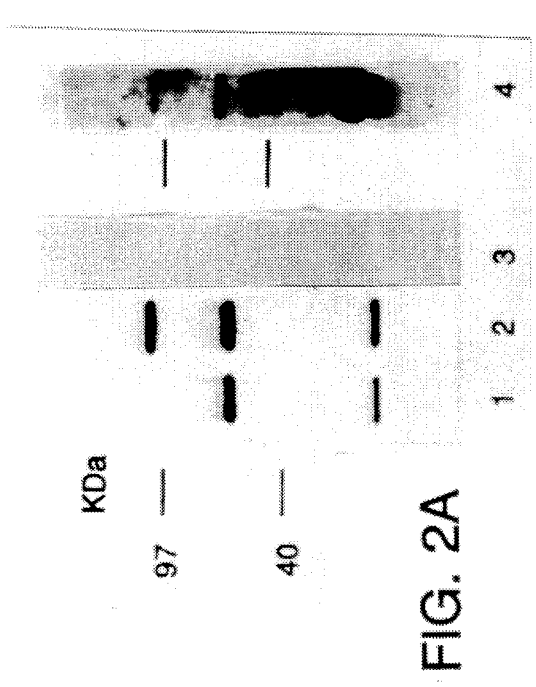

In an effort to determine whether APP is linked to $G_o$ in a native membrane environment, the coprecipitation studies shown in FIG. 2a were performed. Solubilized membranes of bovine brain were first immunoprecipitated by monoclonal anti-APP antibody 22C11, and the immunoprecipitate was then probed by immunodetection with 22C11 (Lane 2) or 1C1, a monoclonal antibody against the C-terminal peptide$_{677-695}$ of APP (SEQ ID NO: 13; Lane 4). Lanes 1 and 3 of FIG. 2a indicate the controls in which either no solubilized membranes were included (Lane 1), or rabbit IgG was used for the precipitation step instead of antibody 22C11 (Lane 3). In each control, immunodetection was performed with 22C11. The 55-kDa and 25-kDa bands seen in Lanes 1 and 2 may be heavy and light chains of the 22C11 used for precipitation, which reacted with an anti-mouse IgG antibody during immunodetection. The precipitate by control rabbit IgG contained no detectable APP. Although the 100 kD molecular size of APP appears here to be slightly less than the 110–130 kD reported (Weidemann et al., Cell 57:115–126, 1989), the precipitated form is unlikely to be an extracellular fragment of APP, because 1C1 recognizes this 100-kDa band.

In the experiment illustrated in FIG. 2b, coprecipitation of various G proteins with APP was investigated. Bovine brain membrane preparations were immunoprecipitated with 22C11; the immunoprecipitated proteins were subjected to SDS-PAGE and immunoblotted with the indicated anti-G protein antisera (1/1000 dilution). Lane 2: GC/2, anti-$G_o\alpha$ antiserum; lane 3:GC/2 plus 1 µg/ml of purified $G_o$; lane 4: GA/1, common $G\alpha$ antiserum; lane 5: AS/7, anti-$Gi\alpha$ antiserum; lane 6: MS/1, common $G\beta$ antiserum. Lane 1 shows a control immunoblot with GC/2, in which a buffer solution rather than the bovine brain membrane preparation was immunoprecipitated with 22C11. Lane 7 indicates immunoblotting with GC/2 of the precipitate resulting from immunoprecipitation of brain membranes with control rabbit IgG, rather than 22C11. The identity of the 39-kDa protein in lane 2 as $G_o$ was verified by its absence in the non-membrane control (lane 1); by its staining with another $G_o\alpha$-specific antibody, αGO1 (Morishita et al., Eur. J. Biochem. 174:7–94, 1988) (data not shown); and by a diminution of staining of this band in the presence of excess soluble $G_o$ (lane 3). The 22C11-precipitate also contained immunoreactivity of $G\beta$ in a doublet at 35–36-kDa (lane 6). The 22C11-precipitate did not react with an anti-$Gi\alpha$ antibody AS/7 (lane 5). The antibody GA/1 detected only a 39-kDa band in the 22C11-precipitate (lane 4). The control rabbit IgG immunoprecipitate did not produce anti-$G_o$-immunoreactive bands corresponding to either APP or $G_o$(lane 7). These experiments indicate that the 22C11-precipitate from brain membranes contains APP immunoreactivity at 100 kDa, $G_o\alpha$ immunoreactivity at 39 kDa, and $G\beta$ immunoreactivity in a doublet at 35–36 kDa, but no detectable immunoreactivity indicating the presence of $G_f\alpha$ or other heterotrimeric G proteins. A tubulin antibody, YL1/2, did not stain the 22C11-precipitate (data not shown).

Figure 2C:
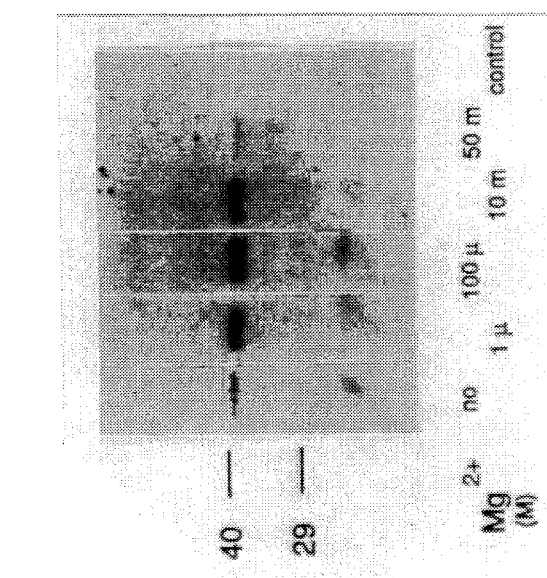

In the experiment shown in FIG. 2c, the effect of $Mg^{2+}$ concentration on co-precipitation of $G_o$ with anti-APP antibody was studied. 100 µg of solubilized brain membranes were precipitated by 22C11 in the presence of various $Mg^{2+}$ concentrations controlled with Mg-EDTA buffer (Birnbaumer et al., J. Eur. J. Biochem. 136:107–112, 1983). The precipitates were analyzed by immunoblotting with GC/2. The control lane indicates the results of precipitation of brain membranes by rabbit IgG followed by immunodetection with GC/2. In the absence of $Mg^{2+}$, $G_o$ was less efficiently co-precipitated by 22C11. $Mg^{2+}$ concentrations between 1 µM and 1 mM resulted in maximal immunoprecipitation of $G_o$. At concentrations >10 mM, relatively little $G_o$ was precipitated. In contrast, immunoprecipitation of APP by 22C11 was not affected by $Mg^{2+}$ concentration (data not shown). These results indicate that, while $Mg^{2+}$ is not absolutely required for complex formation by APP and $G_o$, the concentration of $Mg^{2+}$ does strongly influence complex formation. A mid range of $Mg^{2+}$ concentration was found to facilitate APP-$G_o$ association.

FIG. 2d illustrates the results of an experiment indicating that peptide 20 (SEQ ID NO: 1) prevents the 22C11-mediated co-precipitation of $G_o$, whereas it did not affect the precipitation of APP by 22C11. In contrast, a control peptide (SEQ ID NO: 13) representing a segment of APP different from that represented by peptide 20 (SEQ ID NO: 1) had no discernable effect on 22C11-mediated co-precipitation of $G_o$. In this experiment, solubilized brain membranes were incubated with 22C11-coated beads in the presence of 10 µM peptide 20 (SEQ ID NO: 1; 2nd and 5th lanes) or 10 µM of the control peptide, peptide$_{677-695}$ of APP (SEQ ID NO: 13; 3rd and 6th lanes), or in the absence of both of these peptides (1st and 4th lanes). In this experiment, an anti-mouse IgG antibody different from that used in (a) was employed.

Precipitation of $G_o$ reconstituted with recombinant APP-antibody complex

Figure 3A:
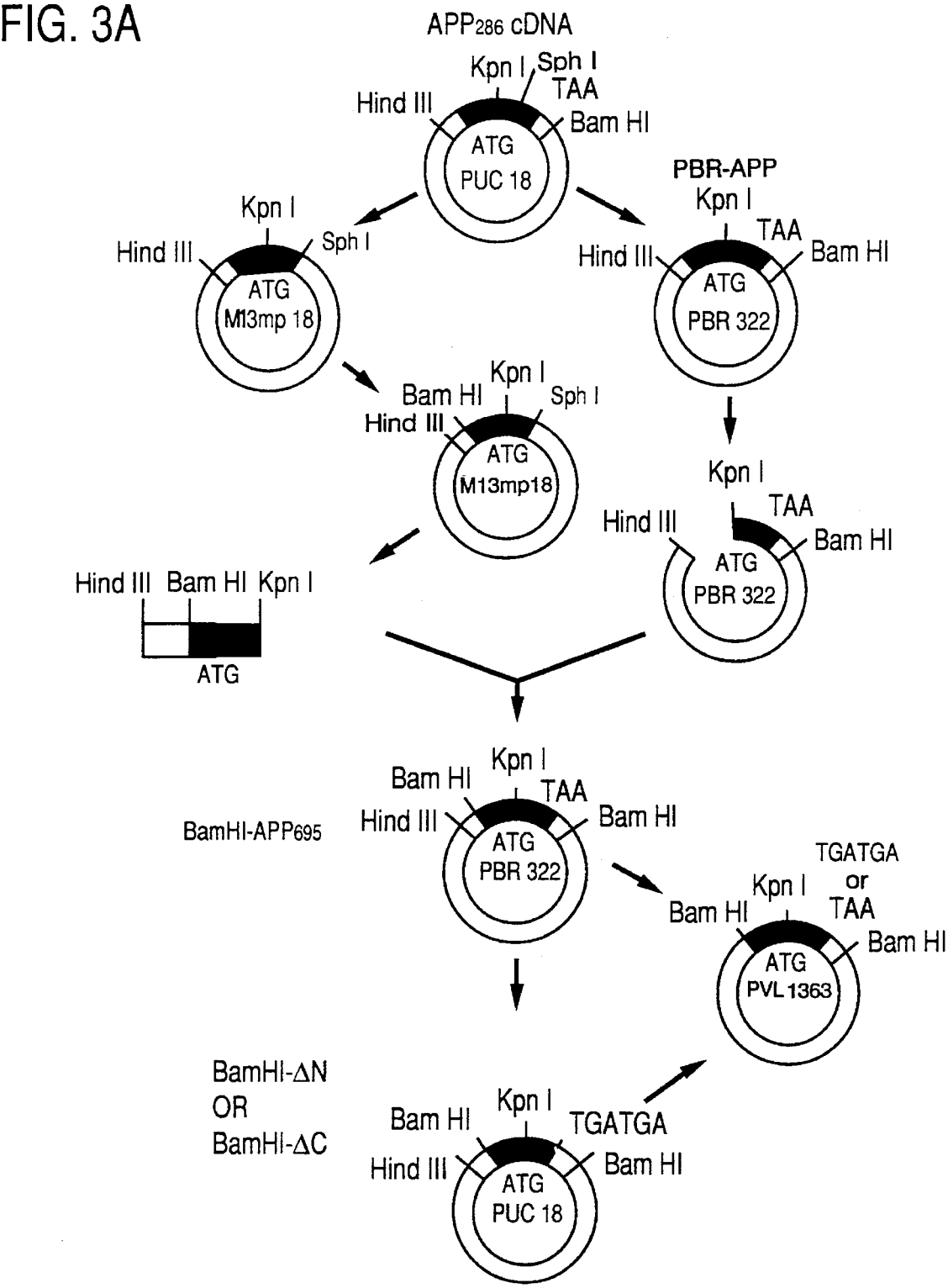
FIG. 3a is a schematic diagram of the construction method used to prepare recombinant mutant APP cDNAs. Regions labeled ATG, TAA, TGA signify original translation and termination sites and a newly inserted termination site, respectively.

A baculovirus DNA encoding full-length APP$_{695}$ (SEQ ID NO: 9) was prepared as outlined in FIG. 3a. Authentic mouse APP$_{695}$ cDNA (SEQ ID NO: 9) was provided by Dr. Yoshiyuki Sakaki (University of Tokyo, Japan) (Yamada et al., Biochem. Biophys. Res. Commun. 149:665–671, 1987) in the vector pUC18. The HindIII-BamHI fragment containing the entire coding region was initially subcloned into the vector pBR322 (pBR-APP). A single BamHI site was inserted immediately before the ATG codon of the HindIII-SphI fragment. This BamHI site was inserted to permit efficient expression of the encoded APP protein in baculovirus-infected cells. The BamHI site-inserted APP$_{695}$-coding DNA (BamHI-APP$_{695}$) was constructed from the HindIII-SphI fragment and pBR-APP, utilizing their internal KpnI sites, and subcloned into pUC18. By using BamHI-APP$_{695}$ as template, two truncation mutants were generated and subcloned into pUC18. These mutants possess an insertion of two TGA codons immediately before (ΔN) or after (ΔC) the peptide 20 sequence. Each BamHI-BamHI fragment of these respective APP-variation-encoding pUC18 plasmids was inserted into the baculovirus transfer/expression vector pVL1393 (Invitrogen). The entire region that had been through a single-stranded intermediate was sequenced to confirm the absence of unwanted nucleotide changes. New insertions were generated by oligonucleotide-directed mutagenesis with a kit (Takara) by the method of Kunkel et al. (Meth. Enzymol. 154:367–382, 1987). For the insertion of a BamHI site, a restriction fragment encoding the ATG start codon was subcloned into the vector M13mp18 and a single stranded template was generated. An oligonucleotide primer (CCACGCAGGATCACGGGATCCATGCTGCCAGCTTG; SEQ ID NO: 19) was used to introduce GGATCC (SEQ ID NO: 20) immediately before the start codon. Following primer extension, the phage was used to transform E. coli strain JM109. Plaques were selected and a single stranded DNA was sequenced. A restriction fragment containing the mutated region was subcloned into pBR-APP. For the insertion of the stop codons, oligonucleotide primers [CAGTACACATCCATCTGATGACATCATGGCGTGGTG (SEQ ID NO: 21) and CGCCATCTCTCCAGTGATGAATGCAGCAGAACGGA (SEQ ID NO: 22)] and the M13mp19 vector were used to introduce two sequential TGA stop codons. Using the method of Summers and Smith (Summers et al., Tex. Agric. Exp. Stn. Bull. 1555, 1987), baculoviruses incorporating these APP cDNAs were generated using selection by immunoblot analysis with 22C11, and recovered by infecting Sf9 cells (Invitrogen). Four days after treatment of Sf9 cells with the viruses, cells were homogenized and suspended in buffer A. After the solubilization of the pellet with buffer B, the supernatant (100 μg) was mixed overnight with 22C11-coated protein G-Sepharose in buffer C plus 2% BSA at 4° C. on a shaker. After centrifugation, the precipitated beads were incubated with purified G$_o$ (1 μg) in buffer C supplemented with 1.1 mM MgCl$_2$ and 2% BSA for 8–24 h at 4° C. on a shaker. After washing four times with ice-cold buffer C, the centrifugation precipitate was subjected to SDS-PAGE, electroblotting, and immunodetection with the first antibodies (1 μg/ml of 22C11; 10 μg/ml of anti-Alz 90; 1/1000 dilution of 1C1; 1/500 dilution of 4G5; 0.1 μg/ml of αGO1) and the second goat anti-mouse or anti-rabbit IgGs conjugated with HRP. (Immunodetection of 1C1 and 4G5, both of which are mouse IgM (κ), was accomplished using as second antibody a mixture of HRP-conjugated anti-rabbit IgG, rabbit anti-mouse IgM and rabbit anti-mouse κ antibodies.)

Figure 3B:
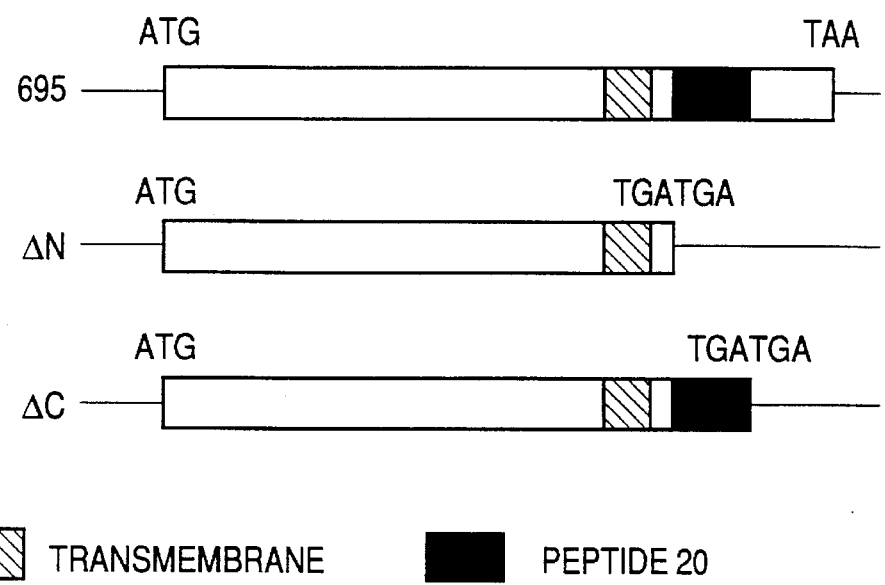
FIG. 3b is a schematic diagram comparing the structures of authentic $APP_{695}$ and the two recombinant mutant APP polypeptides, ΔN and ΔC.

The three APP constructs prepared as described above are compared in the schematic diagram of FIG. 3b. The polypeptides encoded by all three constructs retain the entire transmembrane and extracellular domains of APP; while ΔN (SEQ ID NO: 23) lacks all of the peptide 20 residues as well as the sequence on the carboxy terminal side of the peptide 20 region, ΔC (SEQ ID NO: 24) retains the peptide 20 sequence and is missing only the latter sequence.

Figure 3C:
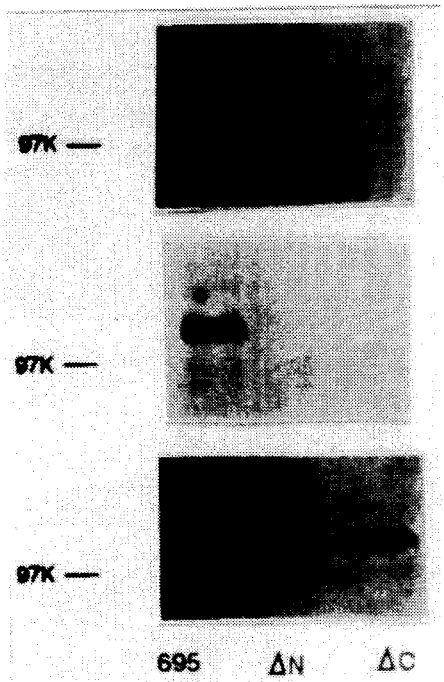
FIG. 3c is an immunoblot analysis of Sf9 membranes using anti-Alz 90, 1C1, and 4G5.

Sf9 cells were infected, using standard methods, by recombinant baculoviruses encoding full length APP$_{695}$ cDNA (SEQ ID NO: 9), APP$_{1-656}$ cDNA (ΔN; SEQ ID NO: 23), or APP$_{1-676}$ cDNA (ΔC; SEQ ID N0: 24). In uninfected Sf9 cells, no immunoreactivity for anti-APP or anti-G$_o$ antibodies was detected (data not shown). The membranes of Sf9 cells infected with the baculoviruses encoding APP$_{695}$ (SEQ ID NO: 9), ΔN (SEQ ID NO: 23), and ΔC (SEQ ID NO: 24) genes (referred to as Sf9-APP$_{695}$, Sf9-ΔN, and Sf9-ΔC, respectively) were found to express, respectively, 130-, 120- and 130-kDa proteins reactive with antibody 22C11 (FIG. 3d, right side). The Sf9-APP$_{695}$ cells expressed APP at ≈0.1% of the total membrane protein. When the membranes of the three types of infected cells were immunoprecipitated with antibody Anti-Alz 90 (Boehringer Mannheim), a mouse monoclonal antibody specific for an epitope corresponding to residues 551–608 of APP (SEQ ID NO: 25; a section of APP that is within the extracellular domain), 130-kDa, 120-kDa, and 130-kDa proteins were recognized in Sf9-APP$_{695}$, Sf9-ΔN, and Sf9-ΔC cells, respectively (FIG. 3c, top panel). Membranes from all three types of infected cells showed approximately equivalent reactivity to the antibody, indicating that at least this portion of the extracellular domain was intact on each of the three and that all three cell types express approximately equal amounts of recombinant protein. When the antibody used was 1C1, a mouse monoclonal prepared against a peptide corresponding to residues 677–695 of APP (SEQ ID NO: 13), only Sf9-APP$_{695}$ membranes were reactive, indicating that the region corresponding to the C-terminal portion of the cytoplasmic domain is missing from both ΔN (SEQ ID NO: 23) and ΔC (SEQ ID NO: 24) (FIG. 3c, middle panel). When the antibody used was 4G5, a mouse monoclonal antibody raised against a peptide corresponding to residues 657–676 of APP (SEQ ID NO: 1; the peptide 20 region of the cytoplasmic domain), 130 kDa bands from both Sf9-APP$_{695}$ and Sf9-ΔC membranes reacted with the antibody, but Sf9-ΔN membranes did not, a demonstration that ΔN (SEQ ID NO: 23) but not ΔC (SEQ ID NO: 24) lacks the peptide 20 region of APP (FIG. 3c, bottom panel). These experiments clearly indicate that the expressed proteins are recombinant APP$_{1-695}$ (SEQ ID NO: 9), APP$_{1-656}$ (SEQ ID NO: 23), and APP$_{1-676}$ (SEQ ID NO: 24), respectively, as designed.

The 22C11-precipitates from these Sf9 membranes expressing various forms of APP were exposed to purified G$_o$, reprecipitated with 22C11, and subjected to immunoblot analysis using anti-G$_o$α antibody αGO1 (FIG. 3d, left four lanes) and by 22C11 (right four lanes). αGO1 (Morishita et al., Eur. J. Biochem. 174:87–94, 1988) was provided by Dr. Tomiko Asano; similar results were obtained when antibody GC/2 was substituted. The control lanes are 22C11-precipitate exposed to G$_o$ in the absence of Sf9 membranes. Approximately 1/10–1/20 (0.05–0.1 μg/tube) of the reconstituted G$_o$ was precipitated, together with a comparable amount (≈0.1 μg/tube) of APP. Easily detectable amounts of G$_o$α were present in the final precipitate when G$_o$ was mixed with 22C11-precipitates from Sf9-ΔC or Sf9-APP695 membranes, but essentially no G$_o$α was found in the final precipitate from Sf9-ΔN membranes. Thus, formation of an APP-G$_o$ complex requires the peptide 20 region, residues 657–676 (SEQ ID NO: 1).

Figure 3E:
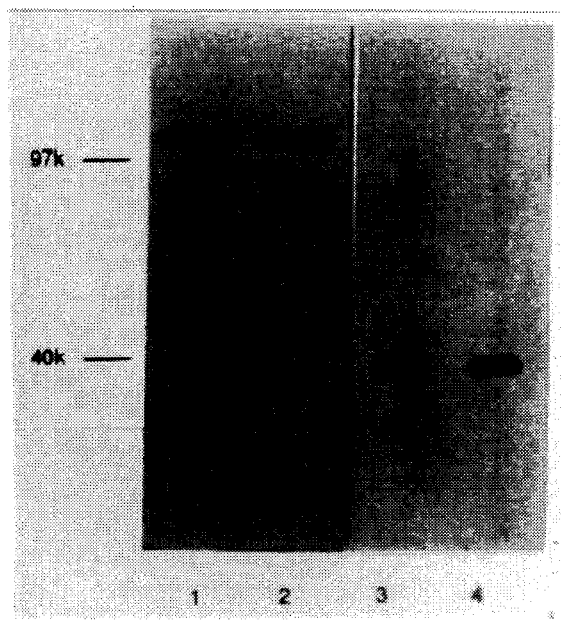
FIG. 3e is an immunoblot illustrating dissociation of $G_o$ from APP by activation of $G_o$. Each of the results presented in FIGS. 3c–e was reproduced at least three times.
Figure 3D:
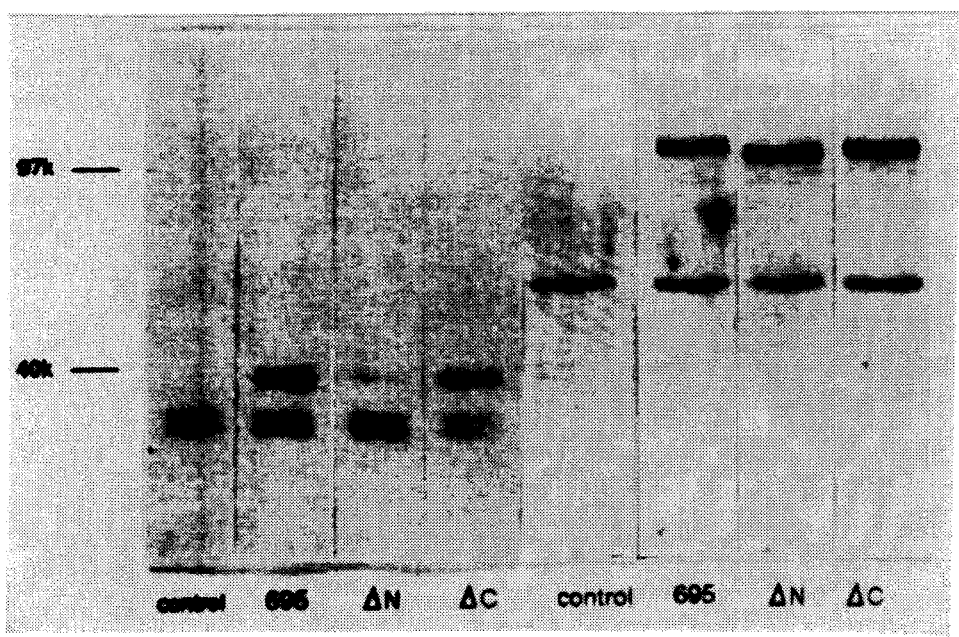
FIG. 3d is an immunoblot analysis of the 22C11-precipitate from an Sf9 membrane-$G_o$ reconstitution mixture.

In the experiment illustrated in FIG. 3e, 22C11-precipitates from Sf9-APP$_{695}$ membranes (100 μg protein each) were incubated with activated G$_o$ (lanes 2 and 4) or unactivated G$_o$ (lanes 1 and 3); the final precipitates (left panel) and supernatants (right panel) were analyzed by simultaneous immunoblotting with 22C11 and αGO1 antibodies. Activation of G$_o$ was carried out by incubating G$_o$ in 20 mM Hepes/NaOH (pH 7.4), 1 mM EDTA, 2 mM MgCl$_2$, and 1 μM GTPγS overnight at room temperature. When G$_o$ was incubated with GTPγS, no G$_o$α associated with the APP-22C11 complex (FIG. 3e), suggesting that the activation state of the G protein regulates APP-G$_o$ association.

This study suggests that APP functions as a receptor coupled to G$_o$ through the G$_o$-activator cytoplasmic domain His$^{657}$-Lys$^{676}$ (SEQ ID NO: 1). APP has a point mutation in at least one form of familial Alzheimer's disease (Goate et al., Nature 349:704–706, 1991). A structural alteration of APP is therefore thought to be one cause of Alzheimer's disease, although it remains unknown how the mutation might produce the disease. One novel possibility suggested by this study is that the cytoplasmic, C-terminal fragment of APP is pathogenic. It has been suggested (Abraham et al., Biotechnology 7:147–153, 1989; Shivers et al., EMBO J. 7:1365–1370, 1988; Kametani et al., Biomedical Research 10:179–183, 1989) that the residual C-terminal portion of APP may remain in the cell membrane after abnormal cleavage of APP to produce β/A4 protein in Alzheimer's disease neurons. By analogy with the oncogenic transformation of c-erb B into v-erb B, such a structural alteration of APP may alter its function and prompt APP to constitutively activate G$_o$. This hypothesis is consistent with the study (Yanker et al., Science 245:417–420, 1989) indicating that recombinant expression of the C-terminal 105-residue portion of APP in neuronal cells evokes cell death, and with the reports that G$_o$ activity is linked to neuronal growth cone motility (Strittmatter et al., BioEssays 13:127–134, 1990), axon and dendrite formation (Granneman et al., J. Neurochemistry 54:1995–2001, 1990), and memory (Guillen et al., EMBO J. 9:1449–1455, 1990). This study suggests that Alzheimer's disease is a disorder of an APP-G$_o$ signalling system caused by structural alterations of APP.

EXAMPLE 1

The screening method of the invention can be carried out as follows:

The assay used can be a very simple cell-free assay employing a first polypeptide consisting essentially of the couplone, or G$_o$-binding portion, of APP (SEQ ID NO: 1) and a second polypeptide consisting essentially of an APP-binding portion of G$_o$. This APP-binding portion of G$_o$ may be the 15-residue segment identified as the anticouplone portion of G$_o$ (SEQ ID NO: 3), or it may be one or both of the two flanking regions, residues 1–3 (SEQ ID NO: 4) and residues 19–36 (SEQ ID NO: 5) of G$_o$. Alternatively, longer portions, or all, of APP and/or G$_o$ can be used, or the appropriate portions of APP and/or G$_o$ can be linked to other polypeptides to form hybrid polypeptides with characteristics (such as altered immunoreactivity or enzymatic activity) that would improve detection of the endpoint of the assay. The assay is carried out by contacting the APP-based polypeptide with the G$_o$-based polypeptide in the presence of a candidate compound, in parallel with a control assay containing no candidate compound, and determining whether the candidate compound inhibits co-immunoprecipitation of the first and second polypeptides (using either an antibody specific for the first polypeptide or an antibody specific for the second polypeptide). Alternatively, activation of the second (G$_o$) polypeptide may be the measured criterion: if so, the second polypeptide must include the GTP-binding region of G$_o$ (SEQ ID NO: 10), and GTP or an appropriate non-hydrolyzable analog thereof (such as GTPγS or Gpp(NH)p) must be included in the assay. The assay may also be carried out using phospholipid vesicles prepared by standard methods (e.g., as described by Nishimoto et al., J. Biol. Chem. 264:14029–14038, 1989), provided that the first (APP) polypeptide includes a region of hydrophobic amino acids [such as all (SEQ ID NO: 8) or a portion (e.g., SEQ ID NO: 7) of the transmembrane region of APP] that permit it to be anchored in the phospholipid bilayer. Alternatively, the assay may be carried out using intact cells or red cell ghosts which contain APP and G$_o$, or appropriate portions thereof. The cells may express the first and second polypeptides naturally or by virtue of genetic engineering, or the polypeptides may be introduced directly into the cells or ghosts by standard means.

EXAMPLE 2

The progress of Alzheimer's disease may be halted or reversed by treating a patient with a compound which diminishes the activation of neural G$_o$ by truncated APP. Such a compound may be identified in a screening assay as described above, or may consist essentially of a polypeptide containing the amino acid sequence of (a) the couplone region of APP (SEQ ID NO: 1), (b) the anticouplone region of G$_o$ (SEQ ID NO: 3), or (c) the APP-associating region(s) of G$_o$ (SEQ ID NO: 4 and/or 5), or a combination of (b) and (c). Such polypeptides may be produced in quantity by standard recombinant means, or by standard synthetic techniques. To minimize proteolytic degradation in vivo, the carboxy and amino termini may be derivatized (e.g., with ester or amide groups), some or all of the amino acids may be replaced with D-amino acids, or particularly sensitive peptide linkages may be substituted with non-peptide bonds using standard methodology. To improve penetration of the blood-brain barrier (BBB), the polypeptides may be altered to increase lipophilicity (e.g., by esterification to a bulky lipophilic moiety such as cholesteryl) or to supply a cleavable "targetor" moiety that enhances retention on the brain side of the barrier (Bodor et al., Science 257:1698–1700, 1992). Alternatively, the polypeptide may be linked to an antibody to the transferrin receptor, in order to exploit that receptor's role in transporting iron across the blood-brain barrier, as taught by Friden et al., Science 259:373–377, 1993. It is expected that an intravenous dosage equivalent to approximately 1 to 100 μmoles of the polypeptide of the invention per kg per day, or an intrathecally administered dosage of approximately 0.1 to 50 μmoles per kg per day, will be effective in blocking activation of G$_o$ in an Alzheimer's patient. If the polypeptide is sufficiently protected from proteolytic degradation, as described above, it may also be administered orally in appropriately higher doses. Alternatively, the compound may be incorporated into a slow-release implant to ensure a relatively constant supply of the therapeutic to the patient's brain.

Other embodiments are within the claims which follow.

5,578,451

I claim:

1. A method of screening for compounds potentially useful for treating Alzheimer's disease, said method comprising:

(a) contacting a first molecule comprising the couplone portion comprising SEQ ID NO: 1 of amyloid precursor protein (APP) with a second molecule comprising one or more of the APP-associating regions of $G_o$ selected from the group consisting of SEQ ID NOs: 3, 4, and 5, in the presence of a candidate compound; and (b) detecting whether a complex forms between said first and second molecules to determine whether said candidate compound inhibits the formation of said complex, said inhibition being an indication that said candidate compound is potentially useful for treating Alzheimer's disease.

2. The method of claim 1, wherein said detection step comprises:

(a) immunoprecipitating said first molecule with an antibody specific for APP; and (b) detecting the presence or amount of said second molecule which co-precipitates with said first molecule.

3. The method of claim 1, wherein said detection step comprises:

(a) immunoprecipitating said second molecule with an antibody specific for $G_o$; and (b) detecting the presence or amount of said first molecule which co-precipitates with said second molecule.

4. The method of claim 1, wherein said first molecule comprises the portion of $APP_{695}$ from residues 649 to 695 (SEQ ID NO: 6).

5. The method of claim 1, wherein said first molecule comprises the portion of $APP_{695}$ from residues 639 to 648 (SEQ ID NO: 7).

6. The method of claim 1, wherein said first molecule comprises the portion of $APP_{695}$ from residues 640 to 695 (SEQ ID NO: 26).

7. The method of claim 1, wherein said first molecule comprises $APP_{695}$ having SEQ ID NO: 27.

8. The method of claim 1 wherein said second molecule comprises the GTP-binding region of $G_o$ having SEQ ID NO: 10.

9. The method of claim 1, wherein said second molecule comprises the GTP-binding region of $G_o$ having SEQ ID NO: 2.

10. The method of claim 1, wherein said contacting step is carried out at a $Mg^{2+}$ concentration between $1\times10^{-7}M$ and $1\times10^{-2}M$.

11. The method of claim 1 wherein said contacting step is carried out in a cell free system.

12. The method of claim 1, wherein said Alzheimer's disease is Familial Alzheimer's disease.

13. A method of screening for compounds potentially useful for treating Alzheimer's disease, said method comprising:

(a) contacting a first molecule comprising the couplone portion comprising SEQ ID NO: 1 of amyloid precursor protein (APP) with a second molecule comprising one or more of the APP-associating regions of $G_o$ selected from the group consisting of SEQ ID NOs: 3, 4, and 5, in the presence of a candidate compound; and (b) detecting activation of said second molecule to determine whether said candidate compound inhibits the activation of said second molecule, said inhibition being an indication that said candidate compound is potentially useful for treating Alzheimer's disease.

14. The method of claim 13, wherein said detection step comprises:

(a) contacting said second molecule with a substrate selected from the group consisting of GTP and a non-hydrolyzable analog of GTP; and (b) detecting or measuring the binding of said substrate to said second molecule, wherein binding of said substrate to said second molecule is indicative of said activation of said second molecule by said first molecule.

15. The method of claim 13, wherein said contacting step is carried out at a $Mg^{+2}$ concentration between $1\times10^{-7}M$ and $1\times10^{-2}M$.

16. The method of claim 13 wherein said contacting step is carried out in a cell free system.

17. The method of claim 13, wherein said Alzheimer's disease is Familial Alzheimer's disease.

18. A kit for screening candidate Alzheimer's disease therapeutics, said kit comprising:

(a) a first molecule comprising the sequence of the couplone portion of APP having SEQ ID NO:1; and (b) a second molecule comprising the anticouplone sequence of $G_o$ having SEQ ID NO: 3; and (c) either
  (i) a means for detecting the formation of a complex by said first molecule and said second molecule, or
  (ii) a means for detecting the activation of said second molecule by said first molecule.

19. The kit of claim 18, wherein said Alzheimer's disease is Familial Alzheimer's disease.

20. A method for screening candidate compounds to identify a ligand for which APP is a receptor, said method comprising:

(a) providing APP and a $G_o$ molecule to form a complex;

(b) contacting a candidate compound with the extracellular domain of said APP, the cytoplasmic tail of said APP being accessible to said $G_o$ molecule, and (c) detecting either
  (i) disassociation of said $G_o$ from said complex, or
  (ii) activation of $G_o$ by said APP molecule in said complex, wherein said dissociation or activation of said $G_o$ is an indication that said candidate compound is a ligand of APP.

* * * * *